United States Patent [19]
Morton

[11] Patent Number: 5,993,828
[45] Date of Patent: *Nov. 30, 1999

[54] TUMOR ASSOCIATED ANTIGEN COMPOSITIONS AND METHODS

[76] Inventor: Donald L. Morton, 24752 Malibu Rd., Malibu, Calif. 90265

[*] Notice: This patent is subject to a terminal disclaimer.

[21] Appl. No.: 08/462,570

[22] Filed: Jun. 5, 1995

Related U.S. Application Data

[63] Continuation of application No. 07/431,533, Nov. 3, 1989.
[51] Int. Cl.$^6$ .......................... A61K 35/12; G01N 33/53; C07K 16/30
[52] U.S. Cl. ................... 424/277.1; 435/7.23; 530/387.7; 530/389.7; 530/828
[58] Field of Search ................................ 530/828, 387.7, 530/389.7; 435/7.23; 424/277.1

[56] References Cited

U.S. PATENT DOCUMENTS

| | | |
|---|---|---|
| 4,233,286 | 11/1980 | Soothill et al. . |
| 4,348,376 | 9/1982 | Goldenberg . |
| 4,557,931 | 12/1985 | Irie et al. . |
| 4,562,160 | 12/1985 | Real et al. . |
| 4,753,884 | 6/1988 | Kit et al. .................................. 435/235 |
| 4,806,628 | 2/1989 | Albino et al. . |
| 4,810,781 | 3/1989 | Hollinshead et al. . |
| 4,895,817 | 1/1990 | Witter ....................................... 424/89 |
| 5,030,621 | 7/1991 | Bystryn . |
| 5,194,384 | 3/1993 | Bystryn . |
| 5,427,664 | 6/1995 | Stoev et al. . |
| 5,484,596 | 1/1996 | Hanna et al. ......................... 424/277.1 |

FOREIGN PATENT DOCUMENTS

| | | |
|---|---|---|
| 306995 | of 0000 | European Pat. Off. . |
| 668350 | 8/1995 | European Pat. Off. . |
| 2140030 | of 0000 | United Kingdom . |
| 2133146 | 7/1984 | United Kingdom . |
| 2188 637 | 10/1987 | United Kingdom . |

OTHER PUBLICATIONS

Bystryn et al., "Preparation and Characterization of a Polyvalent Human Melanoma Antigen Vaccine," *Journal of Biological Response Modifiers*, 5:211–224, 1986.

Dunbar et al., "Protein Analysis Using High–Resolution Two–Dimensional Polyacrylamide Gel Electrophoresis," *Methods in Enzymology*, 182:441–443, 1990.

Euhus et al., "A Murine Monoclonal Antibody to a Glycoprotein Tumor Associated Antigen in Sera and Urine of Melanoma Patients," *AACR*, Abstract No. 1566, 1988.

Euhus et al., "Demonstration and Isolation of a Glycoprotein Tumor Associated Antigen from Sera of Melanoma Patients," *Proceedings of American Society of Clinical Oncology*, Abstract No. 169, 7:44, Mar., 1988.

Euhus et al., "Induction of antibodies to a tumor–associated antigen by immunization with a whole melanoma cell vaccine," *Cancer Immunol. Immunother.*, 29:247–254, 1989.

Gupta et al., "Immunologic Similarity Between Tumor–Associated Antigens Detected in Urine of Melanoma Patients and Those Expressed by Melanoma Cells," *Proceedings of American Society of Clinical Oncology*, Abstract No. C–35, p. 9, Mar. 1984.

Gupta et al., "Increase in Antibody Level to a Tumor Associated Antigen in Melanoma Patients Undergoing Immunotherapy with a Tumor Cell Vaccine," *Proceedings of American Society of Clinical Oncology*, Abstract No. 979, 6:249, Mar., 1987.

Huth et al., "Purification of Antigens From Urine of a Sarcoma Patient by Affinity Chromatography," *Journal of Surgical Oncology*, 18:237–247, 1981.

Paulie et al., "Monoclonal antibodies to antigens associated with transitional cell carcinoma of the human urinary bladder," *Cancer Immunol. Immunother.*, 17:173–179, 1984.

Rote et al., "Determination of Incidence and Partial Characterization of Tumor–Associated Antigens Found in the Urine of Patients Bearing Solid Tumors," *Int. J. Cancer*, 26:203–210, 1980.

Wong et al.,"Demonstration of a Well–Characterized Tumor–Associated Antigen on Melanoma Cell Surface," *Journal of Surgical Oncology*, 38:147–150, 1988.

Balch and Houghton, eds., "Melanoma vaccines," In: *Cutaneous Melanoma*, J.B. Lippincott Company, PA, 42:542–559, 1989.

Embleton et al., "Immunological monitoring in a controlled trial of immunotherapy in stage lib malignant melanoma," *Br. J. Cancer*, 37:497–504, 1978.

Euhus et al., "Association betweem allo–immunoreactive- and xeno–immunoreactive subunits of a glycoprotein tumor–associatedantigen," *Cancer Immunol. Immunother.*, 32;214–220, 1990.

Euhus et al., "Characterization of a 90–100kDa tumor–associated antigen in the sera of melanoma patients," *Int. J. Cancer*, 45:1065–1070, 1990.

Euhus et al., "Effects of melanoma cell vaccine on levels of antibody to a tumor associated antigen in melanoma patients," *Immunology*, Proceedings of AACR, Abstract 28:349, 1987.

(List continued on next page.)

*Primary Examiner*—Paula F. Hutzell
*Assistant Examiner*—Nancy A. Johnson
*Attorney, Agent, or Firm*—Arnold, White & Durkee

[57] ABSTRACT

A method for inducing or enhancing in a human subject the production of antibodies reactive with the polypeptide subunit of Urinary Tumor Associated Antigen having a molecular weight of about 90 to 100 kD after reduction by β-mercaptoethanol and separation by SDS-polyacrylamide gel electrophoresis is disclosed. The method comprises administering to the subject an effective dose of a composition comprising inactivated tumor cells having Urinary Tumor Associated Antigen on the cell surface and at least one tumor associated antigen selected from the group consisting of GM-2, GD-2, Fetal Antigen and Melanoma Associated Antigen.

14 Claims, 15 Drawing Sheets

OTHER PUBLICATIONS

Foshag et al., "Specific cell mediated cytotoxicity in melanoma patients receiving melanoma cell vaccine (MCV) in combination with various biological response modifiers (BRM)," Proc. Amer. Assoc. Cancer Res., 30:344, 1989.

Foshag et al., "T–Cell cytotoxicity in melanoma patients receiving active specific–immunotherapy (ASI) and correlation to clinical outcome," Oncology, 430–431, publication date unknown.

Gupta et al., "Correlation of humoral immune response to a melanoma tumor associated antigen with survival of melanoma patients receiving active specific immunotherapy," Proc. Amer. Assoc. Cancer Res., Abstract, 30:344, 1989.

Gupta et al., "Detection of tumor associated antigen in urine of melanoma patients by allogenic antibody," FASEB Abstract Form, 1987.

Gupta and Morton, "In vitro production of antibodies to a melanoma tumor associated antigen by Epstein–Barr virus transformed human lymphoblastoid cells," Poster Presentation at the Annual Meeting of the American Association for Cancer Research, 1987.

Gupta and Morton, "Immunochemical characterization of fetal antigen isolated from spent medium of a human melanoma cell line," JNCI, 70(6):993–1004, 1983.

Gupta and Morton, "Monoclonal antibody–based ELISA to detect glycoprotein tumor–associated–antigen–specific immune complexes in cancer patients," J. Clin. Lab. Anal., 6:329–336, 1992.

Gupta and Morton, "Studies of a melanoma tumor–associated antigen detected in the spent culture medium of a human melanoma cell line by allogenic antibody. I. Purification and development of a radioimmunoassay," JNCI, 72(1):67–74, 1984.

Gupta and Morton, "Studies of a melanoma tumor–associated antigen detected in the spent culture medium of a human melanoma cell line by allogeneic antidoby. II. Immunobiologic characterization," JNCI, 72(1):75–82, 1984.

Gupta and Morton, "Studies of a melanoma tumor–associated antigen detected in the spent culture medium of a human melanoma cell line by allogeneic antibody. III. Physiochemical properties," JNCI, 72(1):83–92, 1984.

Hämmerling et al., "The Influence of major histocompatibility complex class I antigens on tumor growth and metastasis," Biochimica et Biophysica Acta, 907:245–259, 1987.

Hayashi et al., "Cytotoxic T cell lines recognize autologous and allogenic melanomas with shared or cross–reactive HLA–A," Cancer Immunol. Immunother., 34:419–425, 1992.

Hoon et al., "A prospective randomized trial of immunomodulation with low dose cyclophosphamide (CYP) in patients receiving active specific immunotherapy with melanoma cell vaccine (MCV)," Melanoma, Proceedings of ASCO, 6:212, 1987.

Hoon et al.,"A randomized trial of immunomodulation with varous low dosages of cyclophosphamide in patients receiving active specific immunotherapy with melanonma cell vaccine," Immunology, Proceedings of AACR, 29:413, 1988.

Hoon et al., "Mixed lymphocyte–tumor reaction and delayted type hypersensitivity in patients receiving specific immunotherapy," Immunology, Proceedings of the American Association for Cancer Research, 31:253, 1990.

Hoon et al., "Suppressor cell activity in a randomized trial of patients receiving active specific immunotherapy with melanoma cell vaccine and low dosages of cyclophosphamide," Cancer Research, 50:5358–5364, 1990.

Hoover et al., "Therapy of spontaneous metastases with an autologous tumor vaccine in a Guinea pig model, " J. Surg. Res., 30(4):409–415, 1981.

Hunt et al., "Complement–dependentlysis of tumor cells by a baboon IgM antibody to a tumor–associated antigen," Cancer Immunol. Immunother., 34:377–382, 1992.

Huth et al., "Relationship of tumor–associated urinary antigens to disease recurrence in melanoma patients," Surgical Oncology, 417–419, published date unknown.

Irie et al., "Antibodies to tumor–associated gangliosides (GM2 and GD2): Potential for suppression of melanoma recurence," In: Basic Mechanisms and Clinical Treatment of Tumor Metastasis, 21:371–383, 1985.

Irie et al., "Human monoclonal antibody to ganglioside GM2 for melanoma treatment," Reprinted for The Lancet, 786–787, 1989.

Irie et al., "Humoral immune response to melanoma–associated membrane antigen and fetal brain antigen demonstrated by indirect membrane Immunofluorescence. I," Cancer Immunol. Immunother., 6:33–39, 1979.

Irie et al., "Melanoma, gangliosides and human monoclonal antibody," Human Tumor Antigens and Specific Tumor Therapy, 115–126, 1989.

Irie et al., "Oncofetal antigen: A tumor–associated fetal antigen immunogenic in man," JNCI, 63(2):367–373, 1979.

Katano and Irie, "Human monoclonal antibody to tumor–associated ganglioside GD–2 suppressed growth pf human melanoma in nude mice," Immunol. Letters, 8(4):169–174, 1984.

Kopald et al., "Complement dependent cytotoxicity against tumor cell lines by a purified baboon IgM antibody to a tumor associated antigen," Immunology, Proc. Amer. Assoc. Cancer Res., 30:346, 1989.

Livingston et al., Vaccines containing purified GM2 ganglioside elicit GM2 antibodies in melanoma patients,: Proc. Natl. Acad. Sci. USA, 84:2911–2915, 1987.

Ljungquist, "A New Endonuclease from Escherichia coli Acting at Apurinic Sites in DNA", J. Biol. Chem., 252(9):2808–2814, 1977.

Mitchison, "Immunologic approach to cancer," In: Transplantation Proceedings, 11(1):92–103, 1970.

Morton, "Active immunotherapy against cancer: Present status," Seminars in Oncology, 13(2):180–185, 1986.

Morton et al., "Active immunotherapy of metastic melanoma with melanoma vaccine and immunomodulation," Extended Abstracts, Proceedings of the American Association for Cancer Research, 32:492–494, 1991.

Morton et al., "Active specific immunotherapy in malignant melanoma," Seminars in Surgical Oncology, 5:420–425, 1989.

Morton et al., "Active specific immunotherapy with melanoma cell vaccine and immunomodulation in patients with metastatic melanoma," ASCO Annual Meeting, 1991.

Morton et al., "Active specific immunotherapy with melanoma cell vaccine and immunomodulation in patients with metastatic melanoma," Abstract of presentation at the International Conference on Biological Treatment of Melanoma and Other Cancers, New South Wales, Sep. 5–7, 1990.

Morton et al., "Adjuvant immunotherapy of malignant melanoma: Results of a randomized trial in patients with lymph node metastases," Section VI. Melanoma, pp. 245–249, 1982.

Morton, "Adujvant immunotherapy of malignant melanoma: Status of Clinical Trials at UCLA," *Int. J. Immunotherapy*, II(1):31–36, 1986.

Morton et al., "Clinical results of a trial of active specific immunotherapy with melanoma cell vaccine and immomodulation in metastatic melanoma," *Immunology*, Proc. Amer. Assoc. Cancer Res., 30:383, 1989.

Morton et al., "Clinical results of a trial of immunotherapy with melanoma cell vaccine (MCV) plus biological response modifiers," *7th International Congress Immunology*, Berlin, Abstract, Jul. 30–Aug. 5, 1989.

Morton et al., "Improved survival of patients with metastatic melanoma (MM) receiving active immunotherapy," *American Surgical Association*, p. 83, 1992.

Morton et al., "Immunological factors which influence response to immunotherapy in malignant melanoma," *Surgery*, 68(1):158–164, 1970.

Morton et al., "Long-term survival in metastatic melanoma after active immunotherapy with melanoma cell vaccine and immunomodulation," *Immunology, Proceedings of the American Associationfor Cancer Research*, 31:281, 1990.

Morton et al., "Preliminary results of a randomized trial of adjuvant immunotherapy in patients with malignant melanoma who have lymph node metastases," *Aust. NZ, J. Surg.*, 48(1):49–52, 1978.

Morton et al., "Prolongation of survival in metastatic melanoma after active specific immunotherapy with a new polyvalent melanoma vaccine," *Ann. Surg.*, 216(4):463–482, 1992.

Morton et al., "Treatment of malignant melanoma by active specific immunotherapy in combination with biological response modifiers," 665–683, 1989.

Pharmacia Fine Chemicals AB, "*Gel Filtration Theory and Practice,*", Sweden, pp. 4, 14, 26–27, 1980.

Pharmacia Fine Chemicals AB, "*Ion Exchange Chromatography,*" Sweden, 43–47, 1980.

Ravindranath et al., "An epitope common to ganglioside O–Acetyl–$G_{D3}$ and $G_{D3}$ recognized by antibodies in melanoma patients after active specific immunotherapy," *Cancer Research*, 49:3891–3897, 1989.

Ravindranath et al., "Role of gangliosides in active immunotherapy with melanoma vaccine," *Intern. Rev. Immuno.*, 7:303–329, 1991.

Sidell et al., "Oncofoetal antigen I: A target for immune cytolysis of human cancer," *Br. J. Cancer*, 40:950–953, 1979.

Stenesh, "Dictionary of Biochemistry and Molecular Biology," John Wiley & Sons, New York, pp. 235–236, 1989.

Tai et al., "Human monoclonal antibody against ganglioside $G_{D2}$: use in development of enzyme–linked immunosorbent assay for the monitoring of anti–$G_{D2}$ in cancer patients," *JNCI*, 73(3):627–633, 1984.

Tai et al., "Immunogenicity of melanoma–associated gangliosides in cancer patients," *Int. J. Cancer*, 35:607–612, 1985.

Tai et al., "Monoclonal antibody detects monosialognagliosideshaving a sialic acid alpha2——3–galactosylresidue," *J. Biol. Chem.*, 262(14):6803–6807, 1987.

Tsuchida et al., "Gangliosides of human melanoma," *Cancer*, 63(6):1166–1174, 1989.

Tsuchida et al., "Gangliosides of human melanoma," *JNCI*, 78(1):45–54, 1987.

Urban et al., "Tumor antigens," *Alternative Immunoassays*, 6:77–86, 1985.

Voller and Bidwell, "Enzyme immunoassays," *Annual Review of Immunology*, Annual Reviews, Inc., Palo Alto, CA, 10:617–644, 1992.

Webster's Ninth New Collegiate Dictionary published by Merriam–Webster, Inc. p. 881, 1991.

Wong et al., "Augmentation of anti–fetal antigen antibody levels in melanoma patients undergoing active specific immunotherapy with a tumor cell vaccine," *Melanoma*, Proceedings of ASCO, 7:248, 1988.

Wong et al., "Demonstration of a cell surface fetal antigen in circulating immune complexes of melanoma patients," *Annual Meeting of American Association for Cancer Research*, Abstract, 0727, 1987.

Wong et al., "Documentation of the presence of a melanoma tumor associated antigen on the cell surface," *Immunology and Cytokines*, Proceedings of ASCO, 6:242, 1987.

Wong et al., "Immunochemical characterization of a tumor–associated antigen defined by a monoclonal antibody," *J. Surg. Res.*, 48:539–546, 1990.

Wong et al., "Recovery of a cell surface fetal antigen from circulating immune complexes of melanoma patients," *Cancer Immunol. Immunother*, 27:142–1476, 1988.

Wong et al., "Kd glycoprotein fetal antigen tumor marker in melanoma," *Proceedings of ASCO*, 7:252, 1988.

Yamamoto et al., "Generation of lymphokine activated killer (LAK) cells by low dose IL–2 in the presence of tumor cells," Proceedings of AACR, 29:399, 1988.

Euhus et al., "Detection of a tumor–associated glycoprotein antigen in serum and urine of melanoma patients by murine monoclonal antibody (AD1–40F4) in enzyme immunoassay," *J. Clin. Lab. Anal.*, 3:184–190, 1989.

Euhus et al., "Induction of antibodies to a tumor–associated antigen by immunization with a whole melanoma cell vaccine," *Cancer Immunol. Immunother.*, 29:247–254, 1989.

Rote et al., "Determination of incidence and partial characterization of tumor–associated antigens found in the urine of patients bearing solid tumors," *Int. J. Cancer*, 26:203–210, 1980.

Zhang et al., "Immunochemical and biochemical characterization of two monoclonal antibody–reacting antigens associated with human bladder carcinoma," *Cancer Res.*, 49:6621–6628, 1989.

Reisfeld, "Human tumor–associated antigens defined by monoclonal antibodies," *CRC Critical Review in Immunology*, 5(1):27–53, 1984.

Brown et al., "Structural characterization of human melanoma–associated antigen p97 with monoclonal antibodies," *Chem. Abstracts*, 95(11), Abstract No. 9529x, 1981 and *J. Immunol.*, 172(2):539–546, 1981.

Dippold et al., "Cell surface antigens of human malignant melanoma: definition of six antigenic systems with mouse monoclonal antibodies," *Chem. Abstracts*, 94(3), Abstract No. 13890f, 1981 and *Proc. Natl. Acad. Sci. USA*, 77(10):6114–6118, 1980.

Young et al., "Production and characterization of mouse monoclonal antibodies to human bladder tumor–associated antigens," *Cancer Res.*, 45:4439–4496, 1985.

Bystryn et al., "Preparation and characterization of a polyvalent human melanoma antigen vaccine," *J. Biol. Response Modifiers*, 5:211–224, 1986.

Liao et al., "Difference in cell binding patterns of two monoclonal antibodies recognizing distinct epitopes on a human melanoma–associated oncofetal antigen," *Mol. Immunol.,* 24(1):1–9, 1987.

Marx, "Cancer vaccines show promise at last," *Science,* 245:813–815, 1989.

LeBeau et al., "Chromosomal sublocalization of the human p97 melanoma antigen," *Hum. Genet.,* 72:294–296, 1986.

Hopman et al., "In situ hybridization as a tool to study numerical chromosome aberrations in solid bladder tumors," Dialog Information Service, file 159, Cancerlit, Accession No. 0584557 and *Histochemistry,* 89(4):307–16.

Doneda et al., "In situ hybridization analysis of interstitial C–heterochromatin in marker chromosomes of two human melanomas," Dialog Information Service, file 159, Cancerlit, Accession No. 00714302 and *Am. J. Pathol.,* 135(6):1105–1117.

Gupta et al., "Immunologic similarity between tumor–associated antigens detected in urine of melanoma patients and those expressed by melanoma cells," Dialog Information Service, file 159, Cancerlit, Accession No. 0330339 and *Proc. Annu. Meet. Am. Soc. Clin. Oncol.,* 3:9, 1984.

Gupta and Morton, "Detection of cancer–associated antigen(s) in urine of sarcoma patients," *J. Surg. Oncol.,* 11:65–74, 1979.

Huth et

Rote et al., "Tumor–associated antigens detected by autologous sera in urine patients with solid neoplasms," *J. Surg. Res.,* 29:18–22, 1980.

Huth et al., "Assessment of in vivo effectiveness of tumoricidal chemotherapy and radiation therapy by serial analysis of tumor–associated urinary antigen titers in patients with sarcoma," *Cancer Treat. Rep.,* 65:1037–1042, 1981.

Huth et al., "Relationship between circulating immune complexes and urinary antigens in human malignancy," *Cancer,* 49(6):1150–1157, 1982.

Finck et al., "Excretion of tumor–associated antigen(s) in the urine of patients with colon carcinoma," *J. Surg. Oncol.,* 21:81–86, 1982.

Huth et al., "A prospective postoperative evaluation of urinary tumor–associated antigens in sarcoma patients," *Cancer,* 53(6):1306–1310, 1984.

Gupta et al., "Prognostic significance of urinary antigen analysis by enzyme–linked immunosorbent assay in melanoma patients," *Diag. Immunol.,* 1:303–309, 1983.

Euhus et al., "Measurement of a glycoprotein tumor associated antigen (TAA) using antibodies of different isotypes for a melanoma patients," *FASEB,* Abstract No. 8947, 1988.

Euhus et al., "A murine monoclonal antibody to glycoprotein tumor associated antigen in sera and urine of melanoma patients," *AACR,* Abstract No. 1566, 1988.

Euhus et al. Proceedings of ASCO vol. 7, Abstract No. 169, p. 44, Mar. 1988.

"Basic Mechanisms and Clinical Treatment of Tumor Metastasis", published by Academic Press in 1985, see Irie et al., Chapter 21, pp. 371–384, 1985.

Katano et al. Immunol. Letters 8(4):169–174 (see abstract), 1984.

Zoller, M. Clinical and Experimental Metastasis 6(5):411–29 (see abstract), Oct. 1988.

Cohen et al. Science 262;841–843, 1993.

TUMOR ASSOCIATED ANTIGEN COMPOSITIONS AND METHODS

The present application is a continuation of U.S. Ser. No. 07/431,533, filed Nov. 3, 1989.

This invention was supported in part by NIH grant Nos. 29605, CA 12582 and CA 30019. The U.S. Government may have certain rights.

BACKGROUND OF THE INVENTION

This invention relates generally to tumor-associated antigens, specifically to an antigen found in the urine of cancer patients which can be used for immunodiagnosis, immunoprognosis, and therapy of human cancer.

It is well documented in animal models that cells were changed biochemically and morphologically after neoplastic transformation in vivo. Such transformed neoplastic cells in appropriate doses are capable of inducing protective immunity against tumor development in syngeneic animals when subsequently inoculated with adequate number of viable neoplastic (cancer) cells. The protective immunity was determined to be due to emergence of certain new components that were called tumor-specific transplantation antigens. Expression of similar components, so called tumor-associated antigens, by human malignant tumor cells has been identified by serologic analysis using autologous and allogeneic human sera as the source of antibody. Use of sera from animals immunized with human cancer cells and murine monoclonal antibodies developed against human tumors have added to the definition of additional tumor-associated antigens. However, xeno-polyclonal or murine monoclonal antibody defined antigens on human tumor cells are not necessarily immunogenic in humans. While the physico-chemical properties of almost all of the antigens defined by xeno-polyclonal and murine monoclonal antibodies have been elucidated in great detail, such information is available for only a very few tumor-associated antigens defined by autologous and allogeneic antibodies. The reasons for such paucity have been difficulties in solubilizing adequate amount of the antigens for subsequent purification to homogeneity and the polyclonal nature of autologous and allogeneic antibodies. Without the availability of well characterized tumor-associated antigens that are immunogenic in the host, the importance of these antigens is not fully realized in terms of their application for immunodiagnosis, immunoprognosis and treatment of human cancer.

The tumor-associated antigens in human neoplasms that have been defined by autologous and allogeneic antibodies vary in their distributions. Some are expressed only by individual tumor cell lines or tumors; some are shared by histologically dissimilar tumors including organs where the tumor arises and fetal tissues. The antigens that are expressed only by individual tumors are of limited importance for immunodiagnosis and treatment because tumor cell lines generally do not establish from every single tumor and cannot be applied to another patient. On the contrary, tumor antigens that are shared by different tumors of the same histologic type or by histologically dissimilar tumors can be applied for immunodiagnosis, immunoprognosis and treatment of different patients with different types of cancers.

There are well documented instances to suggest that immunity against growing neoplasm in humans can be enhanced by active immunization with antigen bearing tumor cells. The purpose of such active specific immunotherapy is directed at attempts to enhance the level of anti-tumor immunity beyond that which is naturally induced by the growing neoplasm. It is believed that a growing neoplasm does not induce a maximum immune response in the host to the tumor associated antigens it contains. Most immunotherapy attempts have involved vaccines prepared from whole tumor cells, because progress has been slow in the isolation and purification of human tumor associated antigens. The possibility that living autologous tumor cells could result in tumor growth at the inoculation site has inhibited the use of such vaccines in man. However, tumor cells that express high levels of shared common tumor-associated antigens can be used to immunize different patients (Morton, D. L. et al, In Terry, W. D., Rosenberg, S. A. (eds): Immunotherapy of Human Cancer. New York, Elsevier North Holland, pp 245–249 (1982); Livingston P.O., et al., Int. J. Cancer 31:567 (1983)). The advantage of using such an allogeneic vaccine is two-fold: (1) an immune response induced against the foreign HLA transplantation antigens on the allogeneic vaccinated tumor cells would cause their rejection; (2) this immunization should induce a strong immune response against the shared common cross-reacting tumor-associated antigens to which the human leukocyte antigens (HLA) might serve as a helper function.

Most attempts at immunotherapy in man have been with vaccines composed of inactivated tumor cells, crude extracts or preparations from isolated membranes. Although such preparations may be effective in eliminating progressive tumor growth, there is always the great danger of inactivating the tumor-associated antigens during preparation of the vaccine, unless immunologic reagents and sensitive techniques are available for systemically following the isolation-purification procedure.

Cancer patients who are most likely to respond to an active specific immunotherapy are those who are early in their disease and have minimal residual tumor burden following treatment with other therapeutic modalities (Morton D. L., Seminars in Oncology 13:180 (1986)).

Using lyophilized and reconstituted urine samples of cancer patients and autologous serum as the source of antibody in a complement fixation assay, immunologic reactivity has been observed. The reactivity was abolished by absorption of the sera with tumor cells and not by human normal cells. These observations indicated that immunologically similar antigens were present in the urine samples and tumor cells. Furthermore, the observed reactivity in urine samples of cancer patients who were studied sequentially disappeared after surgical ablation of tumor but reappeared before tumor recurrence, (Gupta, R. K. et al., J. Surg. Oncol., 11:65 (1979)). Because many of the test samples were highly anti-complementary, perhaps due to artifacts arising during lyophilization process, a different method was developed for preparing urine samples for testing. In this study, 24 hour urine samples were obtained from larger numbers of cancer patients and normal controls. The urine samples were concentrated 100-fold by centrifugation and ultrafiltration, and tested by complement fixation using autologous serum as the source of antibody. Ninety-two percent ($55/60$) of cancer patients were positive for the antigens in their urine as opposed to only 7% ($2/27$) normal controls. Antibody activity of the sera reacting to the urine from cancer patients was removed by absorption with biopsied tumor specimens but not with normal skin or muscle suggesting that the antigens detected in urine of cancer patients were tumor associated (Rote, N. S. et al, J. Surg. Res. 29:18 (1980).

In a subsequent investigation, an allogeneic serum that had high titer to antigens in urine was used as the source of antibody. Use of this antibody source in complement fixation revealed that urine samples of 94.7% of cancer patients and 35.1% of normal controls were positive. Again, absorption of the allogeneic serum with tumor cells (autologous to the urine source) removed the antibody activity. However, human normal lymphocytes, skin and muscle cells were ineffective as absorbents. Furthermore, excretion of antigens into urine appeared to depend on the presence of tumor in the patients, because removal of tumor by curative surgery resulted in cessation of the putative antigens excretion. The urine remained negative as long as the patient was free of tumor (Rote, N. S. et al., Int. J. Cancer 26:203 (1980)). However, presence of the antigens in 35% of normal urine indicated a cross-reacting antigenic system which prevented this test from practical use.

Gel filtration chromatography of the concentrated urine revealed that the antigenic activity was present in the first peak of the elution profile. However, when this procedure was performed in the presence of 6M urea, the antigenic activity was found in three different peaks representing various molecular sizes, the majority of the activity being in the first peak. However, because of the polyclonal nature of the allogeneic serum that was used as the source of antibody, it was impossible to determine if the antigenic activity in different peaks represented disassociation product of a large antigenic complex bearing the same epitope or represented different epitopes. Similar results were observed when lyophilized and reconstituted urine was used (Rote, N. S. et al, supra). Thus the antigens in urine of cancer patients recognized by autologous and allogeneic antibody was actually a macromolecular complex and because of polyclonal nature of the antibody, the nature of the specific epitope could not be determined. However, the majority of the evidence suggested that the excretion of antigenic macromolecular complex into urine of cancer patients was dependent on the presence of tumor in the cancer host. Serial measurements of tumor-associated antigens in the urine of cancer patients who received preoperative chemo- and radiation therapy were made by complement fixation. The level of excretion of the antigens into urine as a result of therapy were compared to pretreatment samples and changes were correlated with clinicopathological evidence of in situ tumor cell destruction. Of the 53 cancer patient studied in this manner, 44 had clinicopathologic evidence of tumor destruction induced by the preoperative therapy, and all 44 patients had four-fold or greater rise in the level of urinary antigens during the treatment period. The other nine patients had no evidence of tumor destruction and the antigen titers in these patients remained unchanged. These results suggested that excretion of tumor-associated antigens in urine could be used to assess the in vivo effectiveness of tumoricidal therapy of nonaccessible tumors (Huth, J. F. et al., Cancer Treat. Rep. 65:1037 (1981)). Similar results were observed in patients with colon carcinoma receiving hyperthermia and chemotherapy. Again, the incidence of antigenic activity in urine of apparently healthy individuals was high, i.e. 10% (2/20). (Fink, S. J. et al., J. Surg. Oncol. 21:81 (1982)).

Because allogeneic serum was used as the source of antibody in the complement fixation assay, the possibility existed that part of the immunologic reactivity with urine samples could be due to histocompatibility antigens. Therefore, the serum was absorbed with pooled lymphocytes to remove as much anti-HLA antibodies as possible from the serum. This often added anticomplementary activity to the serum. This problem was obviated by using the serum at a dilution beyond the anticomplementary activity level. However, this resulted in reduced sensitivity of the assay. Furthermore, some of the test (urine) samples by themselves exhibited the anticomplementary activity rendering them unsuitable for detection of urinary antigens by complement fixation. To circumvent these problems, a competitive inhibition enzyme immunoassay was developed. In this assay, reactivity between known amounts of autologous antibody and tumor-associated urinary antigens was competitively inhibited by allogeneic urine (test) samples only if the test samples contained immunologically similar antigens. The results of the assay correlated very well with the results of complement fixation without having to deal with the problem of anticomplementary activity and reactivity due to HLA present in the test urine samples. However, the test lacked specificity because of reactivity with urine of normal individuals. (Huth, J. F. et al., Cancer 47:2856 (1981)).

Analysis of urinary tumor-associated antigens by gel-filtration chromatography consistently revealed that the antigenic complex recognized by autologous and allogeneic antibodies had a molecular mass of greater than 300 kD. This antigenic mass was clearly too large to pass through the glomerular basement membrane of kidney by simple diffusion. There are several reports in literature concerning the development of nephrotic syndrome in cancer patients. Renal biopsies of these patients often demonstrated the deposition of immune complexes within the glomerular basement membrane (Laughridge, L. W. and Lewis, M. G., Lancet 1:256 (1971); Couser, W. G. et al., Am. J. Med. 57:962 (1974)). Thus, it was logical to assume that antigens shed by tumor cells in vivo into circulation would react with specific antibodies to form circulating immune complexes. These immune complexes might deposit in the glomerular basement membrane and cause membrane damage that would allow the passage of high molecular weight antigenic complex into the urine. A relationship between antigen nonspecific immune complexes in circulation of cancer patients and excretion of urinary antigens was observed. Of 36 cancer patients who were positive for urinary antigens, 28 (78%) were also positive for circulating immune complexes at the time of urine collection. Of 24 patients that were negative for circulating immune complexes, 22 (92%) were also negative for urinary antigens. In a cancer patient whose serum and urine samples were studied sequentially during this course of thermochemotherapy, fluctuations in the levels of circulating immune complexes and excretion of urinary antigens were parallel. These results suggested that excretion of urinary tumor-associated antigens into urine of cancer patients was not an isolated phenomenon; rather, immune complex deposition in kidneys appeared to cause glomerular damage which allowed passage of the antigens into the urine, Huth, J. F. et al., Cancer 49:1150, (1982).

In an attempt to determine the applicability of the urinary tumor-associated antigens for prognostication of cancer patients, the antigenic complex was partially purified and used as target antigen in the competitive inhibition enzyme immunoassay. One hundred-fold concentrated urine samples from normal controls and melanoma patients were used to establish the base line, distribution of the antigens, and early detection of subclinical recurrence. The results were expressed as antigen units (ng antigenic protein/mg creatinine/24 hours) for comparison among individuals. The antigen levels in urine of melanoma patients (median=56.5 units, n=56) were significantly higher (p<0.05) than those of normal controls (median=1.9 units, n=56). The 90th percentile for the normal group was 34.3 antigen units. Using this value as the criterion for positivity, 64% (36/56) urine samples of melanoma group were positive for the antigens as opposed to 11% (6/56) of normal controls. Subsequently a retrospective analysis of 58 melanoma patients paired on the basis of disease recurrence and no recurrence after lymphadenectomy revealed a median antigen level of 68 units for the recurrent group and 18.9 for the non-recurrent group. Eighteen of 29 (62%) melanoma patients who had recurrence of their disease and 9 of 29 (31%) patients who remained disease free were urinary antigen positive. These incidences were significantly different (p<0.005) (Gupta, R. K. et al., Diagnostic Immunol. 1:303 (1983)). Though the results of the above investigations confirmed previous observations, the utility of urinary antigen detection assay remained uncertain because of the consistent observation that urine of many (11%) normal individuals had considerable levels of the antigen.

Despite significant progress made in developing assays using tumor markers that are not immunogenic in the cancer host, e.g., CEA, alpha-fetoprotein, prostate specific antigen, etc., there exists a need to diagnose and treat tumors using tumor-associated antigens that are immunogenic in the cancer host. This invention satisfies these needs by providing for the detection of various tumors by detecting U-TAA while avoiding the detection of false positives. In addition, this invention provides antigenic subunits of U-TAA and a vaccine which induces cell mediated specificity for individual determinants on the tumor cell surface, as well as anti-U-TAA antibody production.

DETAILED DESCRIPTION OF THE INVENTION

Figure 1A:
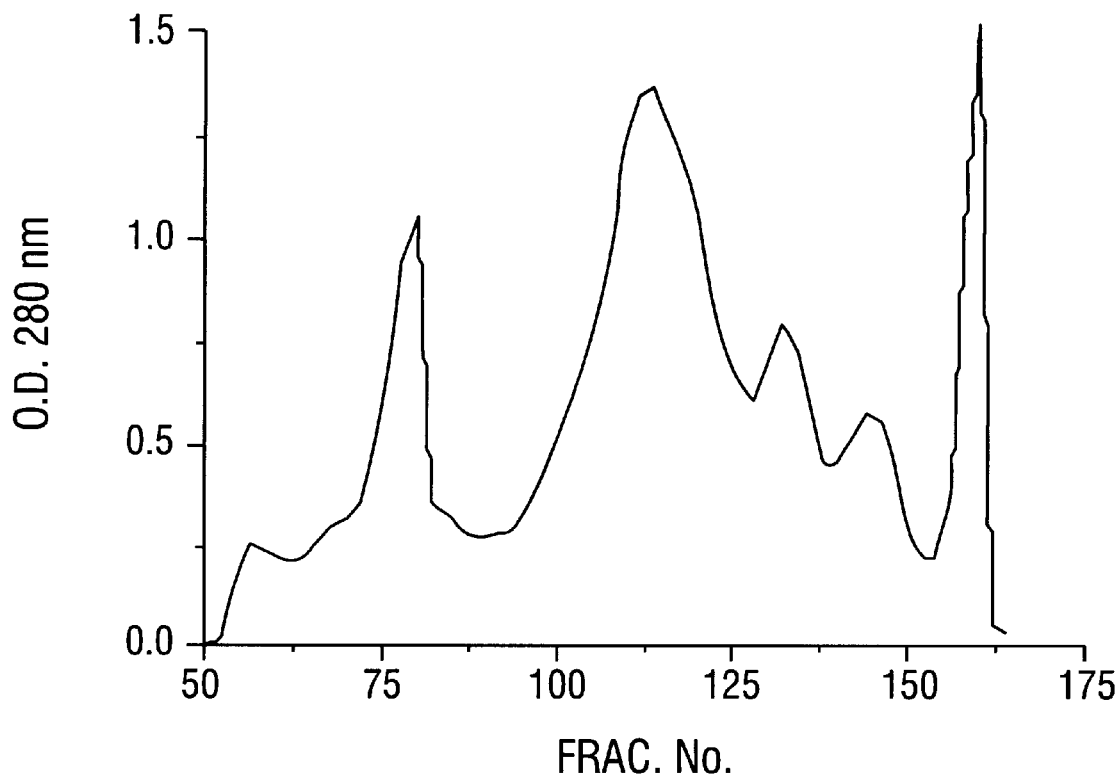
FIG. 1 shows Sephacryl S-200 gel filtration chromatogram of concentrated melanoma urine. Protein content (absorbance 280 nm) and U-TAA activity (ng/100 μl) determined by an allogeneic double determinant EIA are shown.

As used herein, "Urinary Tumor-Associated Antigen (U-TAA)" refers to a high molecular weight glycoprotein that was initially detected in the urine of melanoma patients but subsequently found to occur in other body fluids as well.

In this invention, the antigen U-TAA has been separated from the majority of normal serum proteins by DEAE Sephacel anion exchange chromatography. Even though U-TAA is immunogenic in man, the majority of antigen eluted free of antibody in the second peak of the column. This observation was not surprising as the sera used in these investigations were selected on the basis of high reactivity with the murine monoclonal antibody. Therefore, it is likely that the patients with such high levels of circulating U-TAA were in relative antigen excess and one would expect to isolate antigen free of immunoglobulins. The small amount of U-TAA seen in association with the major IgG and IgM peaks suggested that some anti-U-TAA antibody was present in the form of immune complexes. All urine samples from melanoma patients that were positive for U-TAA using the allogeneic antibody also reacted with the murine monoclonal antibody. The urine samples that were negative in the allogeneic antibody assay were also negative in the monoclonal antibody assay. Furthermore, the monoclonal reacted with the concentrated and partially purified fraction of UCLA-SO-M-14 cultured melanoma cell supernatant. This suggests that immunologically similar antigens excreted into the urine of melanoma patients are also produced by melanoma cells in culture. The monoclonal reactive molecule in melanoma urines shares many characteristics with the allogeneic antibody-reactive U-TAA.

Mixed glycosidase treatment abolished the U-TAA activity of urine samples from normal individuals as measured by the allo-antibody assay. Similar treatment of specimens from melanoma patients, however, significantly augmented the U-TAA activity in the majority of patients. These observations are consistent with the view that the allo-antibody reactive epitope is a protein which resides on a large, variably glycosylated molecule. In this scenario, glycosidase treatment strips carbohydrate from the molecule, exposing additional immunoreactive epitopes.

This theory is further supported by enzyme digestion of the monoclonal reactive epitope. While treatment with hyaluronidase has little effect on the immunoreactivity of the epitope, protease treatment destroys it. Also mixed glycosidase treatment enhances the immunoreactivity of the molecule.

Numerous murine monoclonal antibodies specific for melanoma have been produced by immunizing mice with whole melanoma cells or cell extracts, for example, (Lloyd, K. O., In Basic and Clinical Tumor Immunology, R. Herberman, ed. Nijhoff, The Hague, pp 159–214 (1983)). More uncommon are monoclonal antibodies specific for allo-immunoreactive proteins (Hadas, E. et al., Cancer Res. 46:5201–5205 (1986))

By screening hybridoma supernatants against a panel of melanoma and normal urines, it was possible to identify one clone with specificity for the tumor associated protein. The resultant antibody recognized a protein epitope which occurs with a much greater frequency in the urine and serum of melanoma patients than in that of normal patients. Therefore, the murine monoclonal antibody is significant for immunodiagnosis and immunoprognosis of human cancer.

The invention provides a substantially purified antigenic polypeptide subunit of urinary tumor-associated antigen (U-TAA) having, after reduction by β-mercaptethanol and separation by SDS-polyacrylamide gel electrophoresis, a molecular weight of about 90–100 kD (The subunit was about 90 kD from serum and about 100 kD from urine but represents the same subunit since a murine monoclonal antibody recognizes each subunit.) Urinary tumor-associated antigen has been detected in the sera of 64% of disease-bearing melanoma patients, but rarely in the sera from apparently normal individuals. The antigen purified by DEAE Sephacel anion exchange chromatography is heat stable, has a molecular mass in the range of 590–620 kD under non-reducing conditions and an isoelectric point of 6.1. SDS-PAGE under reducing conditions, resolves this high molecular weight antigen into several components.

The epitope recognized by a murine monoclonal antibody AD1-40F4, is present only on 90–100 kD subunit of the urinary tumor-associated antigen. This subunit, however, contains epitopes recognized by baboon and human polyclonal antisera as well. This has been determined by SDS-PAGE immunoblotting. The epitope recognized by the murine monoclonal antibody is different from those recognized by human polyclonal antibodies.

By contacting the U-TAA from a body fluid of an afflicted subject with the murine monoclonal antibody, the amount of U-TAA per a given amount of body fluid can be compared with an amount previously determined for an equivalent sample; a variation in U-TAA indicates a variation in the state of the malignancy. Thus, monitoring a malignancy refers to the process of repeatedly assaying an afflicted subject's body fluids to determine the amount of U-TAA or the 90–100 kD subunit, present in the fluid. Assays may be performed early in treatment of the patient, as well as during and after treatment. Initially, U-TAA levels may be very high indicating a high turnover or shedding of the antigen. However, after treatment and inhibition of proliferation of tumor cells by vaccination, for example, U-TAA levels in a patient's body fluids may decrease.

The invention allows one to diagnose a tumor in a subject by the method comprising detecting the epitope located on the 45, 65, 90–100, or 120 kD polypeptide from U-TAA in a subject's body fluid after reduction by β-mercaptoethanol and separation by SDS-polyacrylamide gel electrophoresis. The detection can be accomplished by contacting the polypeptide with a reagent and detecting the presence of the reagent which is reactive with the polypeptide.

The invention describes a method of detecting a breast or lung carcinoma in a subject comprising detecting the presence of U-TAA from a sample of the subject. The detection comprises binding the U-TAA with a reagent and detecting the reagent. One example of detection is the binding of U-TAA directly or indirectly by a second reagent. The reagent is preferably an antibody but can be any suitable reagent.

A vaccine is provided for inducing or enhancing antibodies or cell mediated immunity directed against the 90–100 kD polypeptide comprising tumor cells having a U-TAA on the cell surface and at least one tumor associated antigen selected from the group consisting of GM-2, GD-2, Fetal Antigen, or Melanoma-Tumor Associated Antigen, and a pharmaceutically acceptable carrier. Improved results are possible if the tumor cells have HLA of the same type as that of the subject on the cell surface. The vaccine provides a method for inducing or enhancing in a subject afflicted with a cancer the production of antibodies reactive with the polypeptide subunit of U-TAA having a molecular weight of about 90 to 100 kD, comprising administering to the subject an effective dose of the vaccine. The subject of the present invention is a human being, however, any animal may be used. The antibody produced in the individual after administration of the vaccine inhibits or treats the cancer, for example a melanoma. Inhibiting the cancer refers to the ability to contact the tumor cells with a reagent which can prevent the cells from proliferating, thus resulting in cell death and a reduction in size of the tumor. Alternatively, inhibiting can include a direct cytotoxic effect on the tumor cells.

In addition, the invention provides for development of reagents which are reactive with antibodies which are reactive with Urinary Tumor Associated Antigen. These reagents can be anti-idiotype antibodies which refer to immunoglobulins which bear the internal image of the antigen of interest. Idiotypes are antigenic determinants of the antibody combining site, therefore, anti-idiotype antibodies mimic the antigenic epitope of an antigen. The invention provides a method of immunotherapy comprising injecting into a subject a therapeutic amount of the anti-idiotypic antibody. The therapeutic amount is any amount effective to produce a cytostatic or cytotoxic effect on the tumor cells which can readily be determined by one skilled in the art.

The discovery that U-TAA is found on the surface of tumor cells allows a method of treating a tumor expressing U-TAA on the tumor cell surface in a subject comprising injecting into the subject a tumor inhibiting reagent reactive with U-TAA on the tumor cell surface. The reagent may be an antibody and the antibody may be attached to a cytotoxic or cytostatic agent. The cytotoxic or cytostatic agent, for example may be selected from the group consisting of a toxin, radiolabeled moiety, and chemotherapeutic agent.

The invention further provides a method of detecting U-TAA on tumor cells from a biopsy comprising contacting the tumor cells with the murine monoclonal antibody and detecting the bound antibody. Detection methods for the presence of nucleic acid or antigen of the present invention include hybridization of a nucleic acid probe with the nucleic acid of a cell and cell staining with polyclonal or monoclonal antibodies. Such techniques are accomplished by methods well-known to those skilled in the art.

A nucleic acid encoding the polypeptide and a nucleic acid probe capable of selectively hybridizing with the nucleic acid is also provided. The nucleic acid can encode an antigenic portion of the epitopes on U-TAA as determined by the antigenic subunits provided herein. In addition, the nucleic acid can correspond to an antigenic sequence on an anti-idiotypic antibody and a nucleic acid probe capable of selectively hybridizing with the nucleic acid corresponding to the anti-idiotype.

A method of in vivo detection of a tumor in a subject is provided which comprises injecting into the subject a reagent, for example an antibody, reactive with U-TAA on the tumor cell surface, detecting the presence of the reagent which reacts with the U-TAA and thereby detecting the tumor. The tumor may be for example, a melanoma, sarcoma, or carcinoma.

The invention still further provides a method for detecting low levels of U-TAA comprising enhancing the expression of U-TAA in cancer cells with alpha and gamma-interferon, or other biological response modifiers, e.g., retenoic acid, contacting the U-TAA with a reagent and detecting the presence of the reagent. The use of interferon as an anti-cancer agent is currently under intensive investigation. Immune or gamma interferon is produced when sensitized lymphocytes are stimulated with specific antigens. Interferon can be administered to a subject by injection as well. Gamma interferon has been shown to induce, enhance or inhibit the expression of several genes. Among those induced are HLA genes including A, B, C. The expression of HLA genes allows certain cells to be more easily recognized and cleared by the immune system. surprisingly, it has been found that gamma-interferon also enhances expression of U-TAA in some cell lines.

The melanoma tumor cell vaccine (MCV) utilizes allogeneic melanoma cell lines which express four well characterized tumor associated antigens, all of which are widely immunogenic in man. The administration of whole irradiated melanoma cells that express U-TAA does induce anti-U-TAA antibodies of both IgG and IgM isotypes. It is notable that 2-to 5-fold increases in anti-U-TAA IgM titers were detected in 11 of the 15 patients, while IgG responses were seen in only 6 of the 15 patients. Why the IgM response is not consistently translated into an IgG response is not readily apparent. It is probable, however, that the polysaccharide moiety of this large glycoprotein molecule induced IgM antibody by T-cell independent mechanisms. This would result in the production of low affinity IgM in small quantities without a subsequent switch to IgG as observed.

With regard to the specificity of the antibodies induced in response to the MCV, the vaccine should elicit antibodies to an array of antigens associated with melanoma cells comprising the vaccine and the adjuvant. U-TAA that was purified from the urine of a melanoma patient and that is expressed on surface of melanoma cells as the target antigen in ELISA was used. Therefore, antibody activity and its elevation in response to MCV observed in this investigation should be specific to U-TAA. However, to rule out the possibility of non-specific reactivity of the antibodies detected in this investigation, the serum samples from melanoma patients were reacted against KLH as the target antigen. The anti-KLH antibody levels in these patients fluctuated during the course of immunotherapy, but there was no concordance with the elevation of anti-U-TAA antibodies. Furthermore, addition of bovine serum albumin (BSA) to the dilution buffers does affect the antibody levels when U-TAA was used as the target antigen. Thus, despite the polyclonal nature of the serum samples, the elevations in antibody levels observed in this investigation were specific for U-TAA.

A frequent explanation for the transient antibody responses commonly seen with MCV is the induction of T-suppressor cells concomitant with T-helper and B-cell activation. Various immunologic manipulations have been attempted in the past to circumvent this specific suppressor effect with variable success. Cyclophosphamide has been used extensively in this regard and is known to inhibit T-suppressor activation, see for example, Berd, D. et al., Canc. Res. 46:2572 (1986). In this trial, one treatment arm included cyclophosphamide in an effort to combat this very problem. There was no indication that cyclophosphamide influenced the incidence or magnitude of the anti-U-TAA antibody response. However, anti-U-TAA immunity may have been prolonged in the patients receiving this drug.

The antigenic activity of normal urine was completely destroyed by treatment with mixed glycosidases and virtually not at all by proteases. On the contrary, the antigenic activity in melanoma urine was the least susceptible to mixed glycosidase and most susceptible to proteases and carboxypeptidase. These results clearly indicated that the antigenic cross-reactivity of normal urine was due to carbohydrate portion of the urinary tumor-associated antigenic complex of cancer patients. These carbohydrate moieties are present on molecules in normal urine and on urinary TAA complex in urine of cancer patients. Thus, the invention provides a method of detecting or monitoring a cancer in a subject having a urinary antigenic complex resulting from the cancer comprising, removing a sample from the subject, altering the carbohydrate portion of the urinary antigenic complex in the sample so as to prevent binding with reagents which bind to Urinary Tumor Associated Antigen, and detecting at least a portion of the altered urinary antigenic complex and thereby detecting the cancer. By altering is meant any change which prevents or reduces the number of false positives resulting from the reagent binding with the carbohydrate portion of the urinary antigenic complex. Such alteration could, for example, be accomplished by reducing the carbohydrate portion.

The invention also provides two epitopes of Urinary Tumor Associated Antigen located on the 45 kD and 65 kD polypeptide subunits after reduction by β-mercaptoethanol and separation by SDS-polyacrylamide gel electrophoresis, and reactive with autologous human serum. The invention also provides an epitope of Urinary Tumor Associated Antigen located on the 120 kD polypeptide subunit after reduction by β-mercaptoethanol and separation by SDS-polyacrylamide gel electrophoresis and reactive with baboon polyclonal antibodies. The invention also provides an epitope of Urinary Tumor Associated Antigen located on the 90–100 kD polypeptide subunit after similar reducing and reactive with the murine monoclonal antibody provided for herein. The demonstration of four different epitopes is demonstrated by the lack of cross-reactivity between different types of antibodies as taught herein.

The presence of antigenically distinct epitopes allows for a method of detecting Urinary Tumor Associated Antigen in a sample comprising contacting the Urinary Tumor Associated Antigen with a first reagent which binds to an epitope on Urinary Tumor Associated Antigen, contacting the Urinary Tumor Associated Antigen with a second reagent which binds to a second epitope on Urinary Tumor Associated Antigen, binding one of the reagents to a solid support and detecting the presence of the unbound reagent and thereby detecting the presence of Urinary Tumor Associated Antigen. The reagents can be antibodies and the first antibodies can be monoclonal and the second antibodies can be polyclonal. Further, the reagent can be bound to the solid support prior to binding to an epitope on Urinary Tumor Associated Antigen.

The following examples are intended to illustrate, but not to limit, the invention.

EXAMPLE I

Purification of U-TAA from Urine: U-TAA was prepared from the urine of a melanoma patient with disease metastatic to the liver and spleen. The urine was collected over a twenty-four hour period in 0.1 M Tris (pH 8.3) and 0.02% sodium azide as preservatives. Two liters of urine were concentrated to 20 ml using a hollow fiber concentrator with an exclusion limit of 10,000 daltons (Amicon Corp., Danvers, Mass.). Seven ml of the concentrate were applied to a 100×2 cm Sephacryl S-200 column. PBS was used as the eluent at a flow rate of 14.5 ml/hr, and 3.5 ml fractions were collected. The elution profile was monitored at 280 nm. Fractions were assayed for U-TAA activity using allogeneic antibody in a double determinant EIA. Fractions exhibiting the greatest U-TAA activity were pooled and concentrated to 7 ml by ultrafiltration (PM-20 membrane, Amicon Corp., Lexington, Mass.). The concentrate was further purified by incubation with 20% (v/v) rabbit antihuman immunoglobulin immunobeads (Bio-Rad Laboratories, Richmond, Calif.) for 1 hour at 37° C. Protein content of the purified antigen was estimated by the method of Lowry (Lowry, O. H. et al., J. Biol. Chem. 193:265–275 (1951) incorporated by reference herein). Antigen prepared in this fashion was used as a standard or target in immunoassays and as immunogen for production of xenoantibody and murine monoclonal antibody.

Figure 1B:
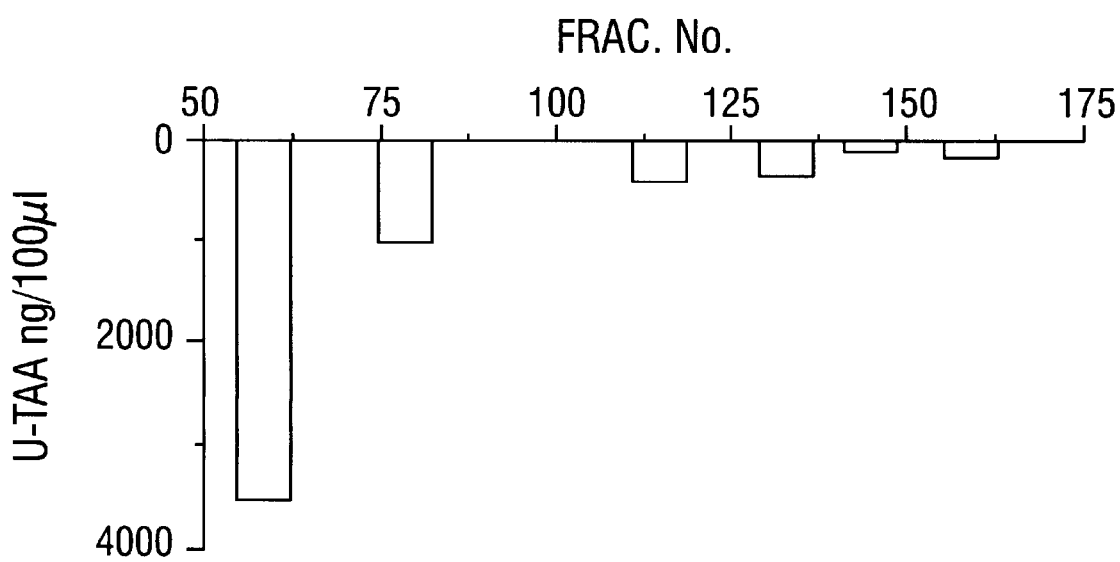

The U-TAA activity of the resultant fractions was measured by the allogeneic double determinant EIA. In this assay, anti-U-TAA IgM was used to capture the antigen and allogeneic anti-U-TAA IgG as the detecting antibody. Though comprising only 0.6% of the total protein, the void volume of the Sephacryl S-200 column contained 63% of all of the U-TAA activity detectable in this urine. This represented a 105-fold enrichment of U-TAA (FIG. 1). Eighteen percent of the U-TAA was detected in the second peak of the chromatogram, but only the first peak was used as target antigen or immunogen in these investigations. A 24-hour urine collection from this patient typically yielded 0.7 mg of U-TAA.

EXAMPLE II

Purification of Human Allogeneic Anti-U-TAA IgM and IgG Antibodies: Initially, IgG and IgM were isolated from the sera of melanoma patients exhibiting high anti-U-TAA antibody levels and were employed in a double determinant EIA for the detection of U-TAA. IgG was isolated by DEAE Affigel Blue chromatography (Bio-Rad Laboratories, Richmond, Calif.). Ten ml of the serum was dialyzed for 48 hrs against 2 liters of 0.02 M potassium phosphate buffer (pH 8.0) with 4 buffer changes. Following dialysis, the serum was centrifuged at 800× g for 15 min. and the supernate passed through a 35 ml bed volume of DEAE-Affigel Blue and eluted with the potassium phosphate buffer. The eluant was collected in 10 ml fractions. The fractions demonstrating absorbance of greater than 0.05 at 280 nm were pooled and concentrated to 10 ml. The allogeneic anti-U-TAA IgG level of the concentrate was measured by an enzyme linked-immunosorbent assay (ELISA). The IgG preparation contained 2.23 mg protein/ml and had an anti-U-TAA titer of 1:2560.

Proteins that remained bound to the DEAE Affigel Blue were eluted with 0.02 M phosphate buffer supplemented with 0.5 M NaCl (pH 8.0) and concentrated to 10 ml. The concentrate was subjected to Sephacryl S-300 (Pharmacia Uppsala, Sweden) gel filtration chromatography to enrich anti-U-TAA IgM antibody. The fractions containing anti-U-TAA IgM antibody activity by ELISA were pooled and concentrated. The IgM preparation contained 0.89 mg protein/ml and had an anti-U-TAA titer of 1:150. These antibodies have been used successfully in a capture assay for U-TAA (Euhus, D., et al., The FASEB Journal 2(6):A1836 (1988)). While the isolated anti-U-TAA IgM and IgG antibodies reacted strongly with the U-TAA, they showed minimal or no reactivity with normal urine components.

EXAMPLE III

Production of Xenogeneic Anti-U-TAA Serum: Anti-U-TAA xenoantisera were prepared in the baboon and were used in ELISA and immunoblotting for the detection of U-TAA. A 12 year old male baboon weighing 28 kg was injected intramuscularly at predetermined (one to four week) intervals with 100 µg U-TAA mixed with an equal volume of Mylanta (Stuart Pharmaceuticals, Wilmington, Del.). The baboon was bled periodically and serum anti-U-TAA levels were measured by ELISA.

After four injections of U-TAA over the course of 6 weeks, the baboon developed detectable anti-U-TAA IgG levels. The antibody titers peaked at the 40th week. At this time the anti-U-TAA antibody titer by ELISA was 1:200,000.

Figure 2:
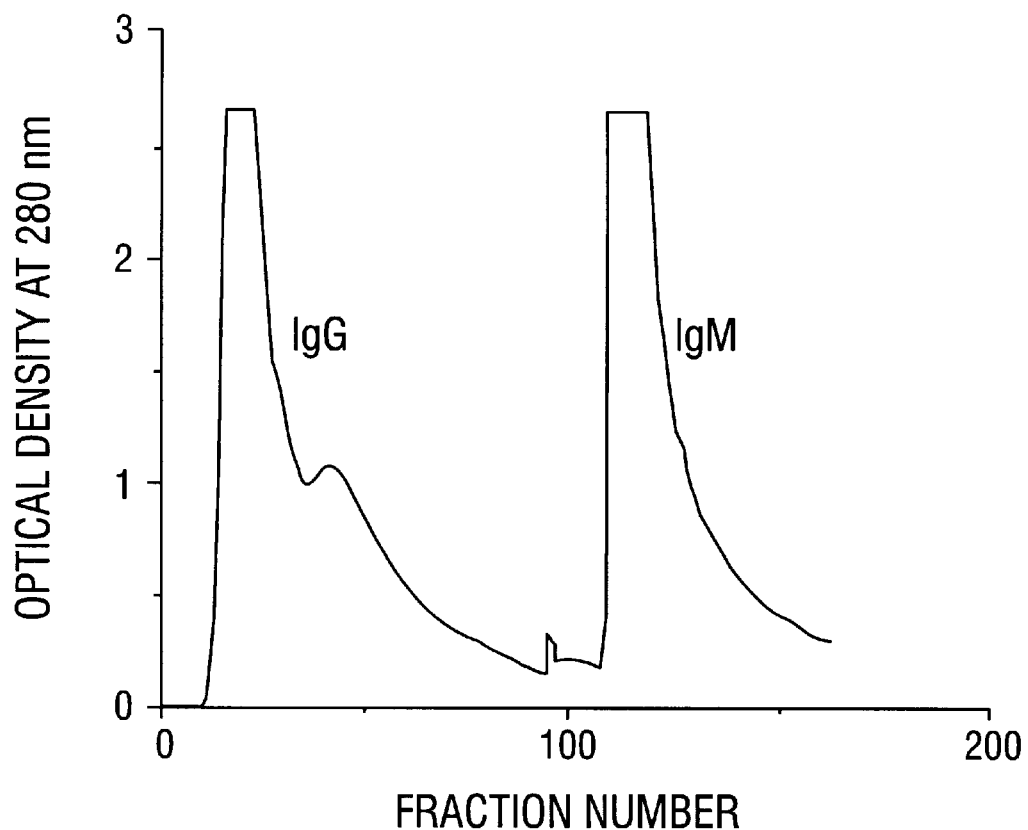
FIG. 2 shows the purification of baboon IgG and IgM antibodies to U-TAA by DEAE Affi-Gel Blue chromatography. The IgG anti-U-TAA antibody was eluted first and IgM anti-U-TAA antibody was eluted with 0.5M NaCl at a flow rate of 60 ml/hr. The pool of fractions comprising IgG had a protein concentration of 3.5 mg/ml and anti-U-TAA titers of 1:250,000. The pool of IgM fractions had a protein concentration of 3.7 mg/ml and anti-U-TAA titer of 1:3600 using purified U-TAA (30 ng/well) as the target.

IgG and IgM antibodies from the baboon serum were purified by DEAE Affi-Gel Blue chromatography as described above in Example II (FIG. 2). IgG antibody was used in the double determinant EIA and IgM for cytotoxicity studies.

EXAMPLE IV

Cytotoxic Effect of Baboon Anti-U-TAA Antibodies: Both IgG and IgM baboon anti-U-TAA antibodies were tested for their cytotoxic effect in the complement dependent cytolysis (CDC) assay using UCLA-SO-M14 as the target. Although the baboon anti-U-TAA IgG antibody was not cytotoxic under the experimental conditions described below, the IgM antibody was cytotoxic.

Target cells (tumor and control) were harvested in mid log phase of growth, washed twice with RPMI-10% FCS, and labeled with 51 Cr. The labeled cells were seeded into the cytotoxicity assay plate at a concentration of 1.0 X 10⁴ cells/well in 50 µl volume. The cells were then mixed with 50 µl of baboon IgM antibody (30 µg protein/ml) and incubated at 4° C. for 1.0 hr, followed by the addition of 100 µl baby rabbit complement at 1:10 dilution. The assay plates were further incubated at 37° C. for 2 hrs. After centrifugation of the plates (500× g for 5 min), 100 µl supernates from each well were aspirated and radioactivity release was assessed by gamma counting. Maximum lysis (total radioactivity added to each well) was determined by adding 150 µl of 0.05% Nonidet P-40 (NP-40) in PBS. The spontaneous release of the isotope was determined from the supernate of those wells that did not receive the antibody. The percentage of cytolysis was calculated from the mean of triplicate well using the following formula:

$$\% \text{ cytolysis} = \frac{\text{CPM with antibody} - \text{CPM without antibody}}{\text{CPM in maximum lysis}} \times 100$$

Figure 3:
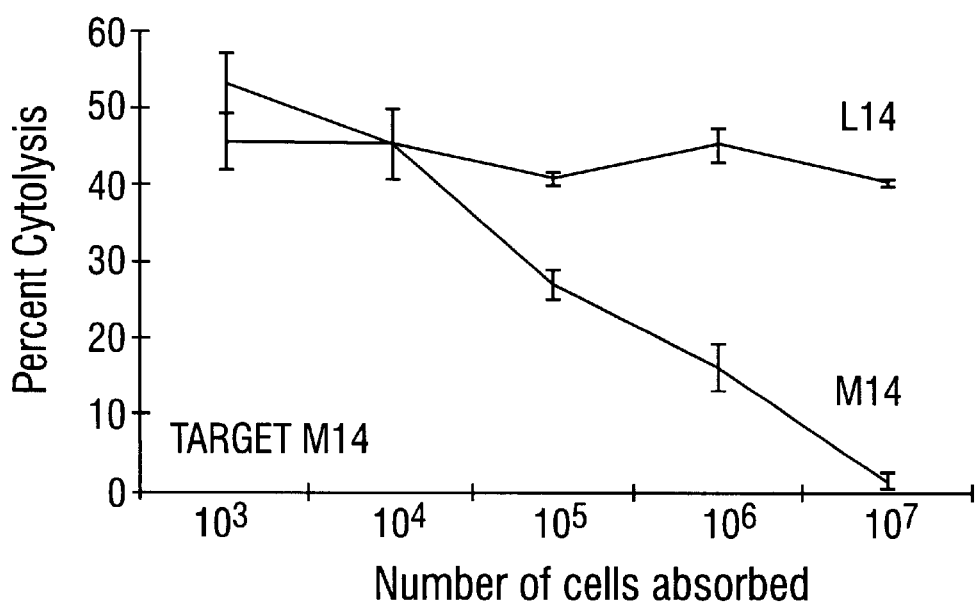
FIG. 3 shows the effect of absorption of baboon anti-U-TAA IgM antibody by UCLA-SO-M14 (M14) and autologous lymphoblastoid (L14) cells on cytolysis in a complement dependent cytotoxicity assay. The cytotoxic effect of baboon IgM anti-U-TAA was completely abolished by absorption with 1×10$^7$ M14 cells and was not affected significantly by the same number of L14 cells.

The cytolysis of UCLA-SO-M14 cells by 50 µl of baboon anti-U-TAA IgM antibody at 1:120 dilution (1.5 µg protein) in CDC was 50 to 60% in contrast to 5% of autologous lymphoblastoid, L14 (normal control) cells. Absorption of the antibody with an increasing number of M14 or L14 cells revealed that, while 1×10⁷ L-14 cells did not affect the cytolysis of M14 cells, absorption with M14 cells decreased the cytolysis with increasing numbers of cells (M14). The cytolysis was abolished by absorption with 1×10⁷ M14 cells (FIG. 3).

Figure 4:
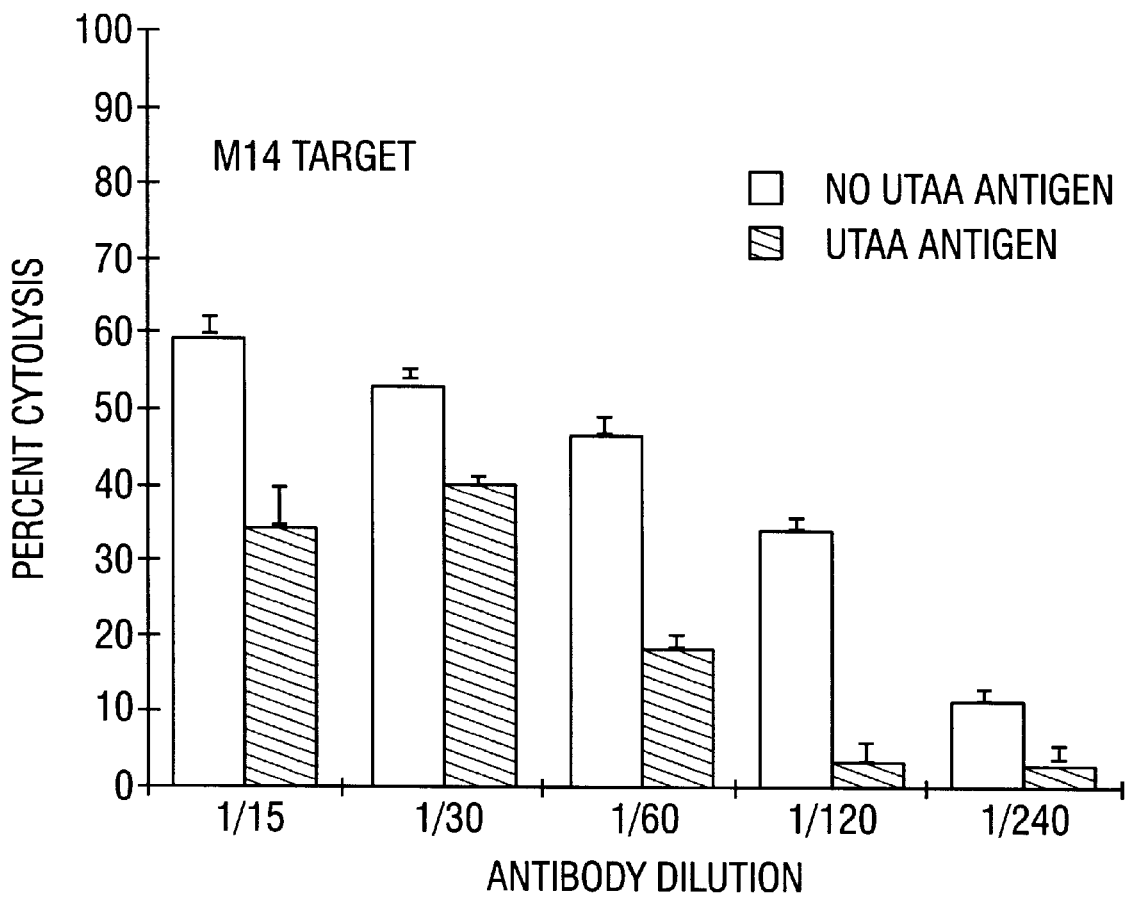
FIG. 4 shows the effect on baboon IgM anti-U-TAA antibody complement dependent assay (CDC) by purified U-TAA. The antibody (3.7 mg/ml) was diluted by RPMI-10% FCS and mixed with an equal volume of U-TAA (0.06 mg/ml) so as to arrive at the indicated final dilution. Purified U-TAA significantly reduced the cytolysis at each dilution of the antibody.

To determine whether the inhibition of cytolysis was due to the expression of U-TAA on the surface of M14 cells, the antibody was mixed at various dilutions with an equal volume of purified U-TAA (0.06 mg/ml) and incubated at 37° C. for 1 hr and then tested in the CDC assay. FIG. 4 illustrates that the cytolysis of M14 cells at 1:120 dilution of the baboon IgM anti-U-TAA was decreased from 35% to less than 5% in the presence of U-TAA. Clearly, purified U-TAA produced the same effect as whole melanoma (M14) cells. Irrelevant proteins, e.g. fetal calf serum (10%), which was included in the assay medium, did not affect the cytolysis.

To determine the cytotoxic effect of baboon IgM anti-U-TAA antibody on cell lines other than M14, various human cultured tumor cell lines, including lymphoblastoid cells, were used as targets in the complement dependent cytotoxicity assay. Tumor cell lines other than melanoma, e.g. breast carcinoma and neuroblastoma, were also lysed by the baboon IgM anti-U-TAA antibody (Table 1). The cytolysis of lymphoblastoid cell line (L 15) was not higher than the background (>5%). These results denote that U-TAA is expressed on the surface of a variety of melanoma and non-melanoma tumor cells and that its density varies from cell line to cell line.

TABLE 1

Cytotoxicity of baboon IgM anti-U-TAA antibody in CDC assay to different target cell lines. (Ten thousand chromium labeled cells of each cell line were reacted with 50 µl [1.0 µg protein] of the antibody in the presence of rabbit complement. Cytolysis was assessed by the release of radioactivity.

| Cell line | Type | % Cytolysis ± SD |
|---|---|---|
| L15 | Lymphoblastoid (normal control) | 4.9 ± 4.9 |
|  | Melanoma |  |
| M9 | " | 40.0 ± 5.0 |
| M10 | " | 71.4 ± 0.4 |
| M14 | " | 68.3 ± 5.6 |
| M16 | " | 20.8 ± 4.0 |
| M24 | " | 36.5 ± 2.8 |
| M101 | " | 25.3 ± 4.6 |
| M109 | " | 29.0 ± 2.7 |
| CPR | Breast carcinoma | 36.5 ± 9.1 |
| MCF | " | 15.0 ± 6.2 |
| CHP | Neuroblastoma | 35.5 ± 1.5 |

EXAMPLE V

Murine Hybridoma Technique: An eight week old brown female C57BL/6 mouse was injected intraperitoneally (ip) with 75 µg of U-TAA (Ne8704) in PBS on days 0, 15, and 28. On day 37, the mouse was boosted with 150 µg U-TAA ip and sacrificed three days later to obtain hyperimmune spleen cells. The cells were fused with 8-azaguanine resistent, non-secreting mouse Sp 2/0 myeloma cells in a manner similar to that described by Galfre (Galfre, G. et al., Nature 277:131 (1979) incorporated by reference herein). Hybridoma cells were seeded onto plates containing 3 day old mouse peritoneal macrophage cultures obtained by rinsing the peritoneum of a C57BL/6 mouse with 5 ml of 11.6% sucrose and plating the macrophages at 1.45×10⁴ cells/well.

Supernatants from wells containing healthy colonies were screened for anti-U-TAA antibody in ELISA. Positive wells were cloned using the method of limiting dilutions. Monoclonal antibody was prepared from mouse ascites (Hoogenraad, N. et al., J. Immunol. Methods 61:317–320 (1983) incorporated by reference herein). Antibody isotypes were determined by double immunodiffusion (Miles Laboratories, Naperville, Ill.).

EXAMPLE VI

Target Antigens for Hybridoma Supernate Screenings: Hybridoma supernatants were tested in ELISA for reactivity with various U-TAA preparations and normal urines. U-TAA was purified from urine samples of three different melanoma patients, Ne8704, Wo7907, and Se8703, by Sephacryl S-200 gel filtration chromatography. Ten normal urines were used as target antigen after 100-fold concentration. Each target was used at 1.4 µg protein/ml. In each case antigen was diluted in 0.06 M sodium carbonate buffer (pH 9.6) and immobilized on microtiter plates by incubation for 3 hr at 37° C. This and each subsequent incubation was followed by three washes in PBS supplemented with 0.05% Tween-20 (PBS-T). Alkaline phosphatase conjugated to goat anti-mouse Ig (Jackson Immunoresearch, West Grova, Pa.) provided the catalyst for conversion of the non-chromogen, P-nitrophenyl phosphate (1 mg/ml in 10% diethanolamine, pH 9.6), to chromogen, P-nitrophenyl. The absorbance of each well was measured at 405 nm using the multiscan ELISA plate reader.

During the course of immunization the anti-U-TAA antibody activity in the mouse serum increased from undetectable to 1:8000 against Ne8704 and 1:7730 against Wo7907 by ELISA. All of the 96 wells seeded with fusion products of the immunized mouse spleen cells grew healthy hybridomas. Supernatants of 51 of these hybrids contained antibody reactive with Ne8704, but only 13 were positive against both Ne8704 and Wo7907. Cells from these 13 wells were cloned. Among the resultant clones, only one designated as AD1-40F4 produced an antibody that reacted with U-TAA of Ne8704, Wo7907, and Se8703 urine samples but not with two concentrated normal urines. AD1-40F4 proved to be an IgM molecule by double immunodiffusion. Unprocessed hybridoma supernatant of this clone had an anti-U-TAA IgM titer of 1:200. AD1-40F4 raised in mouse ascites had an anti-U-TAA IgM titer of 1:2000–1:5000 and was used in subsequent experiments at 1:200–1:500 dilutions.

EXAMPLE VII

Specificity Analysis of AD1-40F4: A murine monoclonal antibody capable of differentiating between U-TAA and normal urine was raised in mouse ascites and tested for reactivity with a variety of immobilized targets (Euhus, D. et al., J. Clin. Lab. Anal. 3:184 (1989)). The ascite was used at 2 µg/ml in all of the following assays. To assess whether the antibody recognized some common human or fetal calf serum protein, the following commercially available proteins were used at 10 µg/ml as targets in ELISA: ferritin, pooled human IgG, pooled human IgM (Cooper Biomedical, Westchester, Pa.), B2-microglobulin, B2-glycoprotein, apolipoprotein B, apolipoprotein CII, and apolipoprotein CIII (Calbiochem, La Jolla, Calif.), human serum albumin (Miles Laboratories, Inc., Naperville, Ill.), and fetal calf serum diluted 1:10. In addition, 20 normal and 52 stage II and III melanoma sera were diluted 1:10, immobilized on polystyrene plates, and then reacted with the antibody. To determine whether the reactivity of the monoclonal antibody correlated with human allogeneic antibody reactivity, 5 melanoma urines positive for U-TAA, 5 melanoma urines negative in the allogeneic double determinant ELISA, and 10 concentrated normal urines were used as targets in ELISA.

Murine monoclonal antibody AD1-40F4 exhibited no reactivity with ferritin, pooled human IgG, pooled human IgM, B2-microglobulin, B2-glycoprotein, apolipoprotein B, apolipoprotein CII, apolipoprotein CIII, or human serum albumin. In addition, it did not react with whole fetal calf serum.

Monoclonal antibody AD1-40F4 reacted with 65% ($33/_{52}$) of randomly selected melanoma sera from stage II and III patients who were alive with disease at the time of serum sampling but with only 5% ($1/_{20}$) normal sera.

Five concentrated urines from melanoma patients testing positive for U-TAA in a human allogeneic double determinant ELISA also demonstrated strong reactivity with AD1-40F4, while five urines that were known to be U-TAA negative failed to react with AD1-40F4.

UCLA-SO-M14 is a cultured melanoma cell line that grows well in chemically defined medium. Concentrated spent media fractionated on a sepharose 6B column was tested in ELISA as the target for murine monoclonal antibody AD1-40F4. The material in the void volume of the column reacted at a dilution of 1:23,000 with AD1-40F4. This dilution corresponded to a protein concentration of 177 ng/ml.

EXAMPLE VIII

ELISA: Target antigen or capturing antibody was diluted in 0.06 M sodium carbonate buffer (pH 9.6) and bound to polystyrene microtiter plates (Immulon I, Dynatech Laboratories, Inc., Alexandria, Va.) by incubation at 37° C. for 2 hr in 100 µl/well aliquotes. The plates were then washed three times with PBS supplemented with 0.05% Tween-20 (PBS-T). Each subsequent reagent was diluted in PBS-T and added in 100 µl aliquotes per well. Each reagent addition was followed by a 45 minute incubation at 37° C. and three PBS-T washes. As the final step, 200 µl of para-nitrophenyl phosphate at 1 mg/ml in 10% diethanolamine (pH 9.8) as substrate for the enzyme was added to each well. The plates were incubated at 23° C. and color development in each well was measured as absorbance at 405 nm using a Multiscan EIA plate reader (Flow Laboratories, Inc., McClean, Va.). Each assay was run in quadruplicate with positive and negative controls, as well as controls for non-specific protein binding and conjugate binding to the immobilized antigen or antibody.

EXAMPLE IX

Double Determinant EIA: Initially, the U-TAA content of fractionated melanoma urine was measured using a double determinant EIA, which employed allogeneic anti-U-TAA IgM and IgG antibodies from melanoma patients. In most subsequent experiments, U-TAA content was measured in a xenogeneic double determinant EIA employing murine monoclonal antibody AD1-40F4 and baboon polyclonal anti-U-TAA IgG.

In the allogeneic antibody assay, microtiter plates were sensitized with IgM (allogeneic) antibody at 20 µg/ml. Serially diluted standards and urine fractions diluted 1:10 in PBS-T were then applied. Allogeneic IgG antibody at 20 µg/ml in PBS-T was added as the second antibody. Alkaline phosphatase conjugated to goat anti-human IgG (Sigma Chemical Co., St. Louis, Mo.) diluted 1:1000 in PBS-T was used as the enzyme conjugate. The absorbance at 405 nm was recorded after a 2 hr incubation with the substrate. The U-TAA concentration of each sample was obtained by interpolation from the standard curve. The assay has a sensitivity of 570 ng/ml.

In the xenogeneic double determinant EIA murine monoclonal antibody AD1-40F4 at 176.0 µg/ml was used to capture the antigen, while baboon IgG at 8.9 μg/ml was used as the second antibody. This assay has a sensitivity of 50 ng/ml.

EXAMPLE X

Sera for U-TAA Activity: Blood was collected by venipuncture from 52 melanoma patients with disease metastatic to regional lymph nodes, in transit lymphatics, or distant visceral tissues and allowed to clot at room temperature for 2 hrs. Sera was separated from the clotted blood by centrifugation at 800× g for 15 minutes and immediately frozen at −35° C. Sera from 20 apparently healthy controls was obtained and processed in a similar manner. On the day of assay, the serum samples were thawed, diluted 1:10 in 0.06 M carbonate buffer, and applied to microtiter plates in 100 μl aliquotes and incubated at 37° C. for 2 hrs. After washing, the wells were reacted with 100 μl of 1:500 dilution of AD1-40F4 MoAb. Bound AD1-40F4 was labeled with goat anti-mouse immunoglobulin conjugated to alkaline phosphatase (Jackson Immunoresearch, West Grove, Pa.) that was diluted 1:5000 in PBS-T supplemented with 1% bovine serum albumin (Sigma Chemical Co., St. Louis, Mo.). Following a 16 hour substrate incubation period, the average absorbance at 405 nm for each sample was determined and corrected for background (binding of AD1-40F4 to plastic and binding of the enzyme conjugate to the target sera). Sixty-three percent ($^{33}/_{54}$) of disease bearing melanoma patients exhibited reactivity with AD1-40F4. In contrast, only 5% ($^{1}/_{20}$) of sera from apparently healthy volunteers exhibited the reactivity. However, the reactivity of this normal serum was minimal.

EXAMPLE XI

Isolation of U-TAA from Serum: A variety of chromatographic and affinity absorption techniques were employed to isolate and characterize U-TAA from the positive serum. Special attention was given to the removal of IgG from the antigen preparation to ensure that AD1-40F4 was recognizing a novel macromolecule and not an idiotypic determinant on an antibody molecule.

Figure 5A:
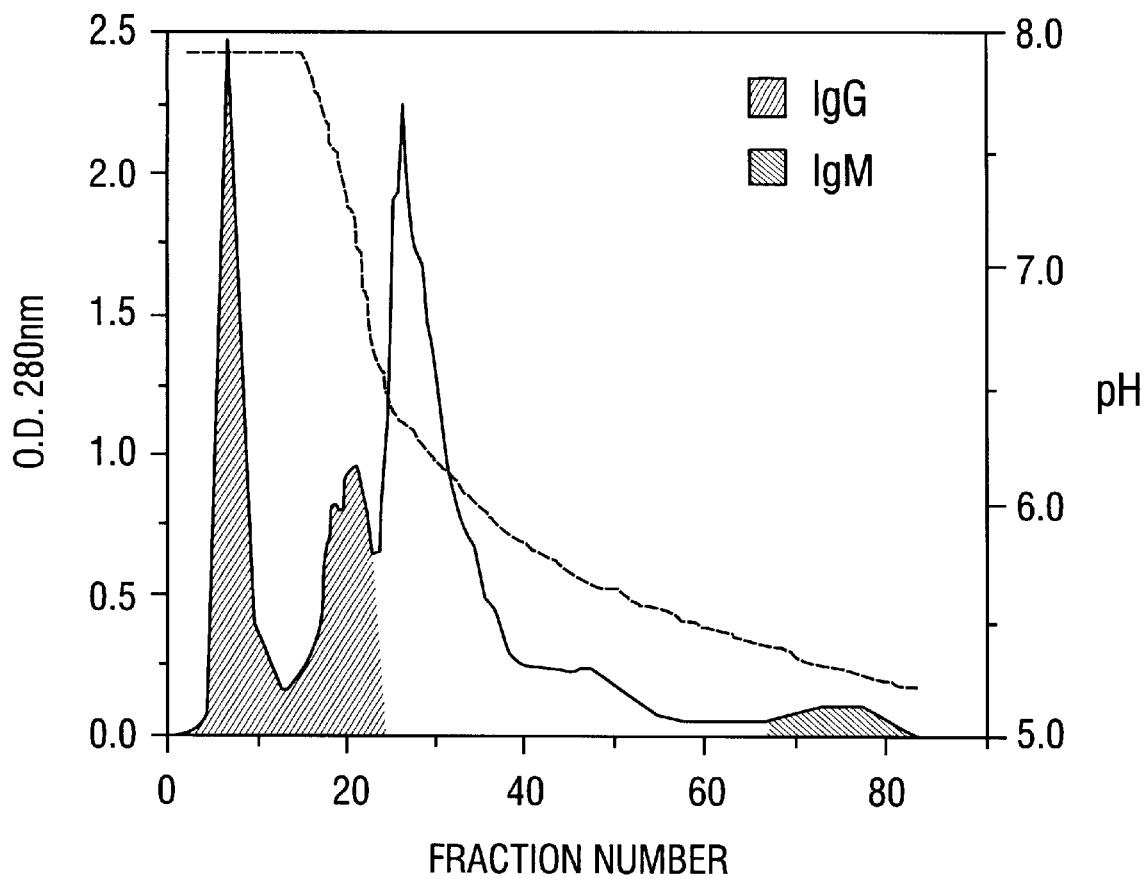
FIG. 5 shows DEAE Sephacel anion exchange chromatogram of AD1-40F4 reactive melanoma serum. Protein content (absorbance 280 nm), presence of IgG, presence of IgM, and U-TAA activity (O.D.$_{405\ nm}$) as determined by a xenogeneic double determinant EIA are shown.
Figure 5B:
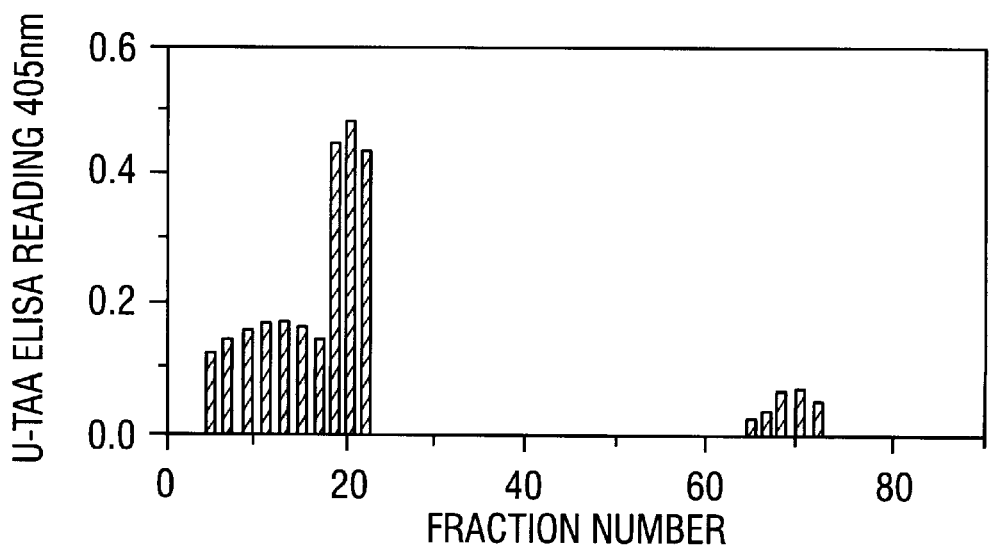

Selected serum samples were applied to a DEAE-sephacel column and eluted at a flow rate of 30 ml/hour with a pH (8 to 5) and salt (0.015 to 0.3M) gradient formed by slowly siphoning 0.3 M $KH_2PO_4$ (pH 5.0) into a vessel containing 200 ml of 0.015 M $K_2HPO_4$ (pH 8.0). Two milliliter fractions were collected and the absorbance at 280 nm and pH of each fraction were determined. The U-TAA activity of fractionated sera was measured using the xenogeneic double determinant EIA described above. Fractions containing the U-TAA activity were pooled and concentrated to 2 ml by ultrafiltration (FIG. 5).

The majority of serum IgG eluted in the first peak of the column; however, small amounts were present in the second peak as well. As expected, IgM was detected only in the last peak. The elution profile of a normal serum was similar to that of a melanoma serum, but no U-TAA was detectable in any fraction. In the U-TAA positive melanoma sera, the antigen was eluted primarily with the second peak, though small amounts were eluted with IgG in the void volume and traces were detected in association with IgM. U-TAA in the second peak eluted at pH 7.27, which corresponds to a $K_2HPO_4$ molarity of 0.021. The anion exchange elution profile of the normal serum that was reactive with AD1-40F4 murine MoAb was identical to that of the serum from melanoma patients, except that no antigen was detected in association with IgM.

Fractions comprising the second peak of the anion exchange column were pooled and concentrated to 2 ml. The. protein content of this preparation averaged 3.78 mg/ml. Because this fraction contained small amounts of IgG, it was absorbed sequentially with rabbit anti-human IgG immunobeads to remove the contaminating IgG. One absorption diminished the IgG titer by 95%, while four absorptions removed 99.5% of the IgG. The U-TAA titer, in contrast, was minimally affected.

U-TAA isolated by anion exchange chromatography and absorbed against anti-human IgG immunobeads was further purified by gel filtration chromatography. The sephacryl S-300 chromatogram consisted of one major protein peak and several minor peaks. The U-TAA activity of antigen positive preparations was consistently confined to a symmetrical high molecular weight peak that was distinct from the major protein peak (this peak was not present in preparations from U-TAA negative sera).

EXAMPLE XII

SDS-polyacrylamide Gel Electrophoresis (SDS-PAGE): Fifty μl of U-TAA from serum at 64 μg/ml was heated to 100° C. for one minute in 25 μl of 0.06 M Tris-HCl (pH 6.8) containing 12.5% glycerol, 1.3% sodium dodecyl sulfate and 1.3% 2-mercaptoethanol. The reduced sample was loaded onto a stacking gel containing 5% polyacrylamide and separated on a 9% polyacrylamide gel at 50 mA for 4 hrs. The running buffer consisted of 0.05 M Tris, 0.38 M glycine, and 0.1% sodium dodecyl sulfate (pH 8.4). All gels were run in duplicate. One gel was stained with silver reagent (Bio-Rad Laboratories, Richmond, Calif.) and the other was subjected to immunoblotting.

EXAMPLE XIII

Immunoblotting: One of the two electrophoresed polyacrylamide gels was washed for 30 min with 0.02 M Tris, 0.15 M glycine and 20% ethanol and electroblotted to nitrocellulose paper (0.45 um, Bio-Rad Laboratories) at 50 Volts for 16 hrs (4° C.). After electroblotting, the nitrocellulose paper was treated with 5% casein in blotting buffer (0.05 M Tris, 0.09 M NaCl, pH 8.0) for 2 hrs at 23° C. The treated paper was reacted with AD1-40F4 (1:500) murine MoAb or baboon anti-U-TAA IgG (1:500) in the blotting buffer supplemented with 5% casein for 6 hrs at 23° C. and then 16 hrs at 4° C. Following incubation with anti-U-TAA antibody, the paper was washed four times in 200 ml blotting buffer. Alkaline phosphatase conjugated to goat anti-mouse Ig or goat anti-human IgG in blotting buffer supplemented with 5% casein was used to detect bound anti-U-TAA antibody. After incubation with the enzyme conjugate at 23° C. for 45 min, the nitrocellulose paper was washed four times with the blotting buffer. After washing again for one minute in substrate buffer (10 mM Tris, 0.1 M NaCl and 0.05 M $MgCl_2$, pH 9.5), the paper was reacted with Nitroblue Tetrazolium Chloride/5-Bromo-4-chloro-3 indolyl phosphate p-toluidine (NBT/BCIP) according to the manufacturer's directions (Bethesda Research Laboratories, Gaithersburg, Md.). The molecular weights of the positive bands were determined based on the relative migration of prestained molecular weight markers (Bio-Rad Laboratories, Richmond Calif.).

EXAMPLE XIV

Figure 6A:
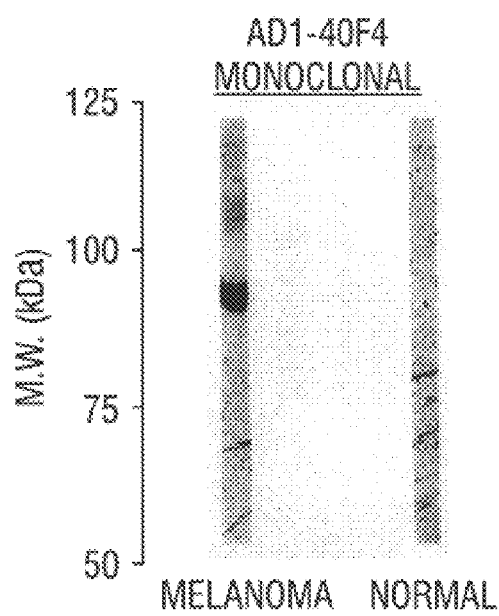
FIG. 6 shows U-TAA purified from the serum of a melanoma patient was separated by SDS-PAGE and then transferred to nitrocellulose paper. Both murine monoclonal and polyclonal baboon anti-U-TAA antibodies recognize a 90 kDa subunit.
Figure 6B:
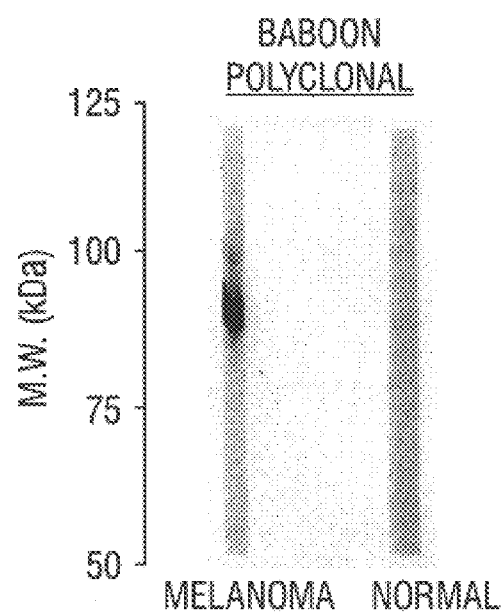

SDS-PAGE Analysis of Serum U-TAA: U-TAA from serum separated by SDS-PAGE and stained with the silver reagent produced four bands in the regions of 138, 90, 50, and 25 kD. When transferred to nitrocellulose paper and immunostained, the 90 kD band was the only one which reacted with both murine monoclonal antibody, AD1-40F4, and baboon polyclonal anti-U-TAA IgG (FIG. 6). U-TAA from the one cross-reacting normal serum exhibited an identical immuno-staining pattern; however, the similar preparation from U-TAA negative normal sera showed no reactivity with either antibody.

EXAMPLE XV

Figure 7A:
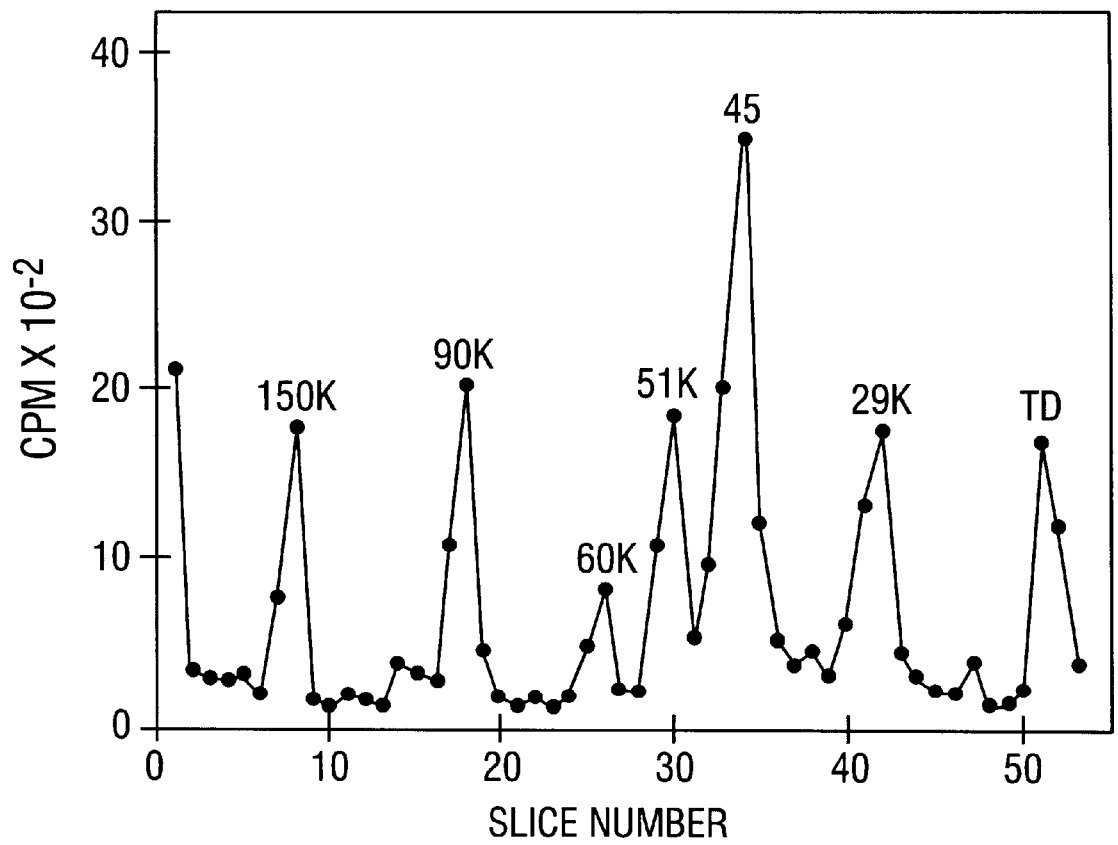
FIG. 7 shows the radioactivity profile in SDS-PAGE of immunoprecipitates formed by reacting the NP-40 extract of biosynthetically labeled ($^{14}$C-L-leucine) melanoma (UCLA-SO-M14) cells with human serum as the source of antibodies. The antibodies were used before (FIG. 7B) and after (FIG. 7B) pretreatment with purified U-TAA. The radioactivity profile was determined by analyzing the radioactivity in 1.0 mm slices of each lane of the gel. Pretreatment of the antibodies (FIG. 7B) showed fewer radioactive peaks, particularly in the 150 to 60 KD and 45 KD regions.
Figure 7B:
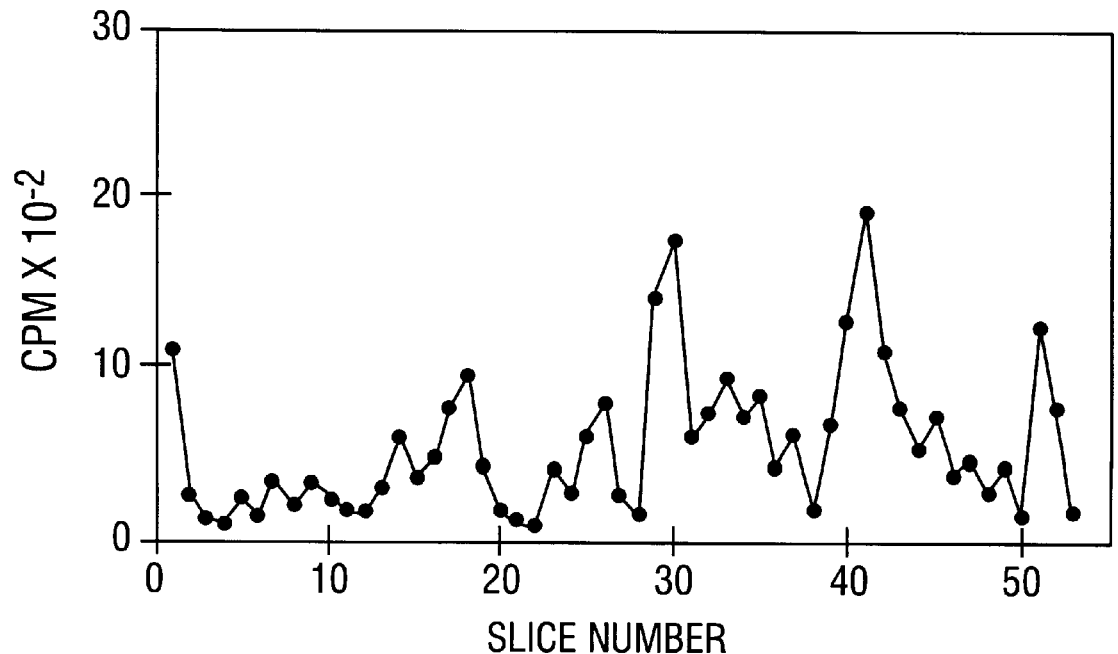

Presence of U-TAA Subunits on Tumor Cells: To determine the expression of the 90 kD component which is recognized by allogeneic antibody, cell free NP-40 extract of biosynthetically labeled ($^{14}$C-L-leucine) melanoma (UCLA-SO-M14) cells was subjected to immunoprecipitation with the allogeneic antibody before and after blocking with U-TAA. The U-TAA (blocker) was purified from the urine of melanoma patients as described in Example I. The NP-40 extract of melanoma cells was prepared as described in Example XXXII. The immunoprecipitates were subjected to SDS-PAGE (12% polyacrylamide). Radioactivity in blocked and unblocked immuno-precipitate lanes of the gel was assessed by scintillation counting. As depicted in FIG. 7, three bands, 150 kD, 90 kD and 45 kD, were partially or completely blocked by U-TAA. These results document that the allogenic antibody reacted with multiple antigenic components of melanoma cells. One of these was a 90 kD subunit that is also present in the urine and serum of melanoma patients and is recognized by the murine monoclonal antibody AD1-40F4.

EXAMPLE XVI

Isoelectric Focusing: Isoelectric focusing of serum U-TAA was performed in a 5% polyacrylamide gel using an LKB 2117 Multiphor system (LKB Instruments, Inc., Rockville, Md.). A strip of filter paper was soaked in 25 μl of U-TAA and placed 1 cm from the cathode edge on the PAG plate (LKB Instruments, Inc.), which contained 2.4% (w/v) ampholine solution with a pH gradient of 3.5–9.5. $H_3PO_4$ (1 M) and NaOH (1 M) were used at the anode and cathode, respectively. The plate was electrofocused by application of 1500 volts, 50 mA, and 30 watts for 1.5 hours at 10° C. Commercially available chromogenic proteins of known isoelectric point (Pharmacia Fine Chemicals, Piscataway, N.J.) were included in each run. A portion of the gel was cut and stained with coomassie blue. However, because the protein content of the U-TAA preparations was quite low (64 μg/ml) coomassie blue staining did not visualize the U-TAA bands. To overcome this difficulty the remainder of the gel was analyzed by the Western blot technique.

Figure 8:
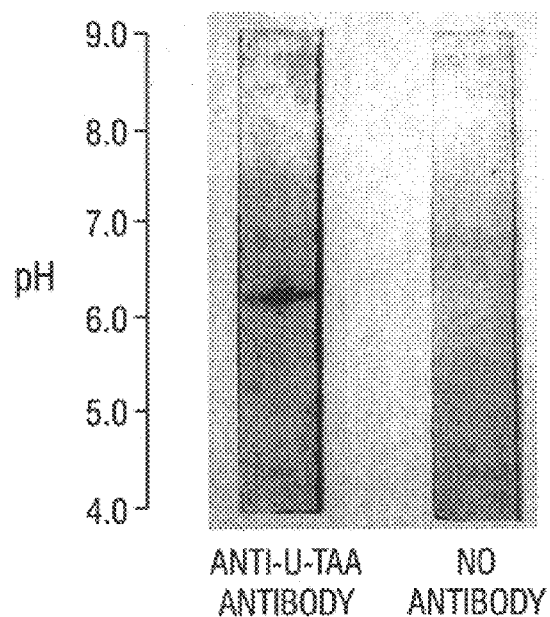
FIG. 8 shows isoelectric focusing of U-TAA purified from the serum of a melanoma patient. After isoelectric focusing, the proteins were blotted onto nitrocellulose and stained with baboon polyclonal anti-U-TAA antisera. A single band corresponding to an isoelectric point of 6.1 was identified.
Figure 9:
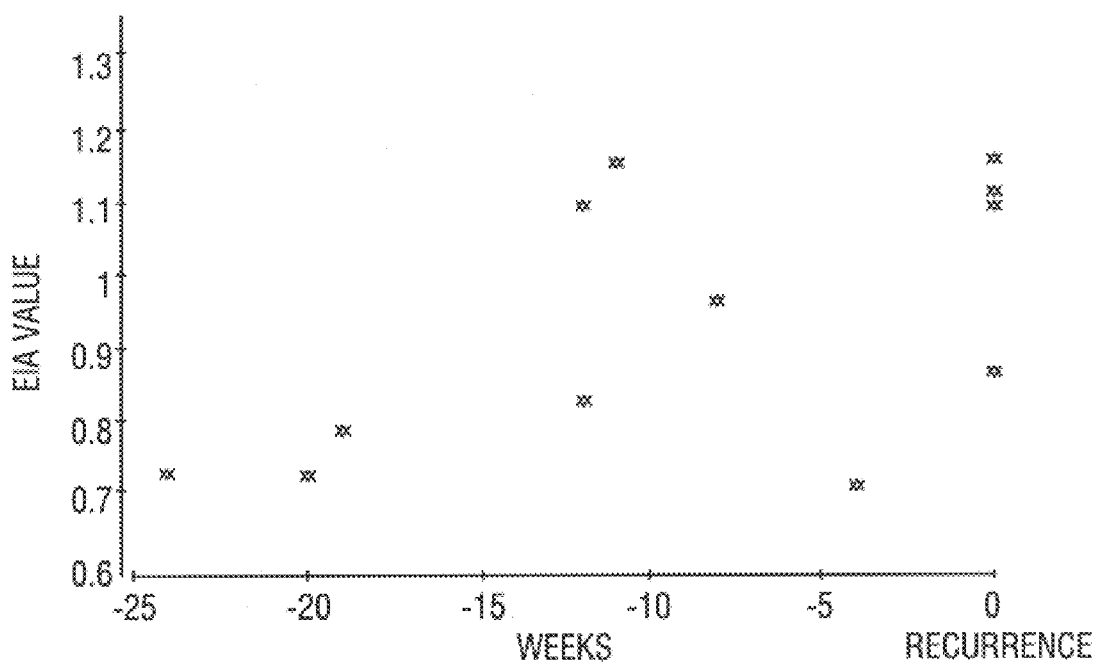
FIG. 9 shows the time difference between the appearance of U-TAA in the urine of surgically treated melanoma patients and the clinically detectable recurrence of the disease.

Focused gels were blotted onto nitrocellulose and reacted with baboon anti-U-TAA IgG. Only one band was visualized by this technique, making it possible to assign an isoelectric point of 6.1 to U-TAA purified from the serum (FIG. 8).

EXAMPLE XVII

Heat Stability: To assess the heat stability of the immunoreactive epitope, U-TAA preparation was heated to 100° C. for 15 min and for one hr. This preparation, as well as the corresponding unheated preparation, was used at 1.4 μg/ml as target for the antibody.

Heating the solution to 100° C. for up to 1.0 hr did not affect the antigenic activity significantly (Table 2).

TABLE 2

Heat Stability of U-TAA Isolated From Serum of a Melanoma Patient

| Treatment | Absorbance at 405 nm in Xenogeneic Double Determinant EIA |
| --- | --- |
| Control[a] | 0.635 ± 0.035[b] |
| 100° C. for 15 min | 0.578 ± 0.042 |
| 100° C. for 1 hr | 0.594 ± 0.065 |

[a]U-TAA was heat treated at a protein concentration of 200 μg/ml and used in the assay at 1.4 μg/ml as the target antigen.
[b]Mean ± standard deviation of triplicate samples.

EXAMPLE XVIII

Enzyme Digestions: To assess the effects of glycosidase digestion on the U-TAA activity of normal and melanoma urines as determined by the allogeneic double determinant ELISA, mixed glycosidase (Miles Scientific, Naperville, Ill.) were coupled to CNBr-activated Sepharose 4B (Pharmacia, Uppsala, Sweden) according to the manufacturer's specifications. The activity of the immobilized glycosidase was assessed by recording hydrolysis of a standard p-nitrophenyl-2-D-glucuronide solution. Twenty-four hour urine specimens were collected from 14 individuals (7 apparently healthy, 7 stage II melanoma alive with disease) in 0.1 M Tris (pH 8.3) supplemented with 0.1% sodium azide. Initial volume and creatinine content (Beckman Creatinine Analyzer, Fullerton, Calif.) were determined for each specimen prior to 100-fold concentration in a recirculating hollow fiber concentrator with an exclusion limit of 10,000 daltons (Amicon Corp., Lexington, Mass.). Concentrated urines were treated with enzyme charged gel (or unlabeled gel prepared in an identical fashion and blocked with 1M ethanolamine) for 4 hrs at 37° C. Treated and untreated urines were then tested for U-TAA activity in the allogeneic double determinant ELISA described above. Results (U-TAA ng/100 ml) were converted to antigen units (Ag U)/mg creatinine to compensate for differences in initial urine volume and interassay variation as follows:

$$\mathrm{AgU/mg\ creat} = \frac{[\mathrm{U\text{-}TAA}] \times F \times 100}{[\mathrm{creat}] \times K}$$

where Ag U/mg creat is antigen units per mg creatinine, [U-TAA] is U-TAA concentration of the sample in ng/ml interpolated from the standard curve. F is the final volume of the 100-fold concentrated urine sample; [creat] is creatinine content (in mg) of the entire 24-hr urine sample and K is the protein concentration (ng/ml) of the U-TAA standard producing an O.D. at 405 nm of 1.0 in this assay. This concentration is arbitrarily assigned a value of 100 antigen units.

Urine samples from seven apparently healthy donors had a mean U-TAA content of 21.9±4.0 antigen units/mg creatinine (by alloantibody assay), while sample from seven stage II melanoma patients alive with disease had a mean U-TAA content of 69.8±17.4 antigen units/mg creatinine (P<0.025). Mixed glycosidase treatment of specimens from normal donors lowered the mean antigen level slightly to 14.8±2.8 P>0.1, while similar treatment of melanoma urines significantly augmented these antigen levels to 163.7±49.4, P<0.025.

EXAMPLE XIX

Characterization of Murine Monoclonal Antibody (AD1-40F4) Reactive Epitope: To elucidate the chemical nature of the AD1-40F4-reactive epitope, U-TAA was degraded with various enzymes immobilized on agarose beads. Mixed glycosidase (Miles Scientific) and hyaluronidase (Worthington Biochemical, Freehold, N.J.) were coupled to CNBr activated agarose beads (Sepharose 4B, Pharmacia Fine Chemicals, Uppsala, Sweden). The immobilized protease was purchased from Sigma Chemical Co. (St. Louis, Mo.). The specific activity of each immobilized enzyme was tested against the appropriate substrate system before treatment of the antigen.

U-TAA at 36 μg/ml was continuously mixed end-over-end for 4 hrs at room temperature with an equal volume of packed-immobilized enzyme beads. CNBr activated agarose beads (without enzyme) blocked with 1M ethanolamine, were used as untreated control. U-TAA activity of the enzyme treated and untreated supernatants was assessed in a competitive inhibition assay as follows: Treated and untreated U-TAA were diluted to 0.63 μg/ml and incubated for 45 min at 37° C. with AD1-40F4 murine monoclonal antibody ascites diluted at 1:375. Binding of the AD1-40F4 in this mixture to immobilized U-TAA was then quantitated in an ELISA. Following correction for non-specific binding to plastic and target antigen, the absorbance at 405 nm was converted to percent inhibition. Each assay was run in triplicate and an average percent inhibition ± SEM was calculated. The inhibitory activity of enzyme treated antigen was compared with that of untreated antigen in a simple ratio (% inhibition treated/% inhibition untreated). These ratios provided a basis for comparing the effects of the three enzymes on U-TAA.

One would expect that treatment of U-TAA with an enzyme that does not affect the immunoreactive epitope would result in an activity ratio near 1.0:1. This was the case with hyaluronidase treatment, where the activity ratio of treated to untreated antigen was 1.5:1. The treatment with glycosidase enhanced the antigen activity (ratio of 3.2:1), while protease treatment significantly diminished the U-TAA activity resulting in a ratio of 0.2:1. Prolonging the protease incubation time by 8 hrs destroys all U-TAA activity.

EXAMPLE XX

Patients: Serum samples from 15 patients undergoing active specific immunotherapy with the MCV were collected prior to immunization and every 2 to 4 weeks thereafter for analysis of anti-U-TAA antibody levels. Seven of the 15 patients evaluated had received cyclophosphamide with their MCV. Samples were also collected from 7 unvaccinated Stage II and III melanoma patients for comparison. The samples were stored at −40° C., and all samples for a given patient were thawed and analyzed on the same day. To ensure that at least half of the subjects were capable of mounting an antibody response to cell membrane antigens, patients were chosen on the basis of their antibody response to M-TAA; eight of the 15 patients had demonstrated induction of anti-M-TAA antibodies during the course of vaccination, while 7 did not. This also allowed us to determine whether antibody response to one membrane antigen guaranteed antibody response to other antigens on the same cell surface.

Vaccination Protocol: First vaccination comprised of 24 million live, irradiated tumor cells (from cell lines designated UCLA-SO-M10 (ATCC designation CRL-12269, deposited Jan. 23, 1997), UCLA-SO-M24 (ATCC designation CRL-12270, deposited Jan. 23, 1997) and UCLA-SO-M101 (ATCC designation CRL-12271, deposited Jan. 23, 1997) which were selected for their antigenic variability) mixed with 24 million Glaxo BCG organisms. Second vaccination consisted of a mixture of 24 million live, irradiated tumor cells and 12 million Glaxo BCG organisms. Subsequent vaccinations consisted of 24 million live and irradiated tumor cells without BCG. The immunization schedule consisted of biweekly vaccinations for the first six weeks and every four weeks thereafter.

Statistical Analysis: Antibody titers in various groups are expressed as means ± standard error of the mean (SEM). Relevant comparisons were made using students' paired T-tests and Chisquare analysis. The statistical software employed in these analyses was StatView (Brain Power, Inc., Calabasas, Calif.) for the Macintosh computer.

EXAMPLE XXI

Determination of Serum Anti-U-TAA Antibody Titers: Forty nanograms of U-TAA in 100 μl of 0.06M carbonate buffer (pH 9.6) was dispensed into 96-well polystyrene microtiter plates. Following a 3 hour incubation at 37° C., the wells were washed 3 times in PBS-T, and 100 μl of serially diluted serum was applied. After a 45 minute incubation at 37° C., the wells were washed and anti-U-TAA antibody was detected using alkaline phosphatase conjugated to goat anti-human IgG (diluted 1:500) or IgM (diluted 1:1000). The plates were incubated for 45 minutes and washed 3 times in PBS-T. Substrate was applied and after a one-hour incubation at 23° C., the $O.D._{405\ nm}$ was determined for each well. All assays were run in duplicate with appropriate controls for non-specific binding of the conjugate to plastic and target antigen. Titration curves were generated by plotting the average corrected $O.D._{405\ nm}$ for the duplicate samples against the serum dilution ($\log_2$). The linear portion of the titration curve was extrapolated and the serum dilution corresponding to an O.D. of 0.05 was designated as the anti-U-TAA "titer" of that particular sample.

EXAMPLE XXII

Anti-U-TAA IgM Antibody Response in Melanoma Patients: There was no significant difference in the anti-U-TAA IgM titers in non-vaccinated melanoma control patients and MCV patients prior to receiving the vaccine (1:1324±254, N=7, 1:1138±198, N=15, P>0.375). However, these levels were significantly lower in a group of 8 apparently healthy donors. Pre-vaccination anti-U-TAA IgM titers ranged from 1:112 to 1:2466 in the 15 patients who received the MCV (Table 3). Eleven of the 15 patients receiving MCV demonstrated a 2 to 5-fold increase in these titers during the course of vaccination. Mean IgM anti-U-TAA titers for these 11 patients rose from 1:1051±259 pre-vaccination to 1:2518±576 post-vaccination (P<0.005). Individual peak anti-U-TAA IgM titers ranged from 1:435 to 1;5140.

EXAMPLE XXIII

Anti-U-TAA IgG Antibody Response: Pre-vaccination anti-U-TAA IgG titers in the 15 MCV patients ranged from 1:1062 to 1:8361 (Table 3). The mean pre-vaccination titer of 1:3984±602 in this group of patients is higher than that of the 7 unvaccinated melanoma control patients (1:2595±423, P<0.1). The mean anti-U-TAA level for 8 apparently healthy controls was significantly lower than that of the unvaccinated melanoma control group. Six of the 15 patients receiving the MCV demonstrated a 2 to 7-fold rise in anti-U-TAA IgG titers. Mean anti-U-TAA IgG titers in this group of 6 responders rose from 1:2964±1046 prevaccination to 1:9958±2677 post vaccination (P<0.01). Individual peak titers in this group ranged from 1:2,176 to 1:20,481.

HLA antibody response during the course of vaccination. Before vaccination, this patient had undetectable anti-HLA antibody levels but high anti-U-TAA IgG levels (1:5056).

TABLE 3

Anti-U-TAA IgM and IgG responses in 15 patients receiving melanoma cell vaccine (MCV)

| | | | IgM | | | | IgG | | | |
|---|---|---|---|---|---|---|---|---|---|---|
| PATIENT | [a]CTX | [b]M-TAA | [c]PRE-MCV | [d]POST-MCV | [e]WEEKS TO RESPONSE | [f]RESPONSE DURATION | PRE-MCV | POST-MCV | WEEKS TO RESPONSE | RESPONSE DURATION |
| 1 | + | − | 1,200 | 1,049 | — | — | 3,200 | 4,045 | — | — |
| 2 | + | − | 877 | 736 | — | — | 2,445 | 3,635 | — | — |
| 3 | − | + | 1,696 | 3,529 | 2 | 4 | 5,056 | 7,270 | — | — |
| 4 | + | − | 1,011 | 2,445 | 8 | 4 | 1,587 | 1,869 | — | — |
| 5 | + | − | 1,562 | 1,421 | — | — | 7,987 | 20,481 | 20 | >10 |
| 6 | + | − | 112 | 515 | 12 | >8 | 4,915 | 5,990 | — | — |
| 7 | + | + | 218 | 448 | 8 | >8 | 5,348 | 3,599 | — | — |
| 8 | + | + | 1,466 | 5,140 | 4 | 4 | 2,274 | 14,848 | 4 | >36 |
| 9 | − | − | 1,411 | 5,043 | 20 | >20 | 2,816 | 7,578 | 40 | >4 |
| 10 | − | + | 464 | 1,261 | 6 | 4 | 1,062 | 2,176 | 8 | 4 |
| 11 | − | + | 1,866 | 1,933 | — | — | 2,496 | 7,680 | 40 | >4 |
| 12 | − | − | 134 | 435 | 12 | 4 | 8,361 | 8,456 | — | — |
| 13 | − | + | 2,278 | 4,992 | 16 | 4 | 1,149 | 6,982 | 8 | >40 |
| 14 | − | + | 384 | 1,152 | 4 | >20 | 6,066 | 6,651 | — | — |
| 15 | − | + | 1,389 | 2,742 | 16 | 8 | 4,992 | 6,349 | — | — |

[a]MCV along (−) or with cyclophosphamide (+);
[b]patient exhibiting good anti-M-TAA response (+);
[c]reciprocal mean prevaccination antibody titer;
[d]reciprocal post-vaccination peak titer;
[e]weeks for MCV to induce >2-fold rise in antibody titer;
[f]number of weeks in which >2-fold elevation in antibody titer persisted

EXAMPLE XXIV

HLA Studies: To assess whether anti-HLA antibodies could account for part or all of our observed antibody responses, the following experiments were performed. First, to mitigate the possibility that our U-TAA preparation was contaminated with HLA, U-TAA was immobilized on polystyrene microtiter plates and tested for reactivity with a murine monoclonal anti-HLA antibody in an EIA (AXL 859M, Accurate Chemical and Scientific Corp., Westbury, N.Y.). This antibody is directed against a monomorphic epitope which occurs on the 45 kD polypeptide products of the Class 1 HLA. Thus, any Class 1 subtypes present in the U-TAA preparation would be detected. A murine monoclonal anti-U-TAA antibody diluted 1:750 was run simultaneously as a positive control.

Secondly, as part of a study to determine the relationship between induction of anti-tumor antibodies and anti-HLA antibodies, 8 pre- and postvaccination sera of melanoma patients who received a melanoma cell vaccine (MCV) were tested for anti-HLA antibodies in a cytotoxic antibody assay that quantitates reactivity with the individual Class 1 and DR antigens (Terasaki, P. I. et al., Manual of Tissue Typing Techniques, DHEW Publ. (NIH) 74–545 U.S. Government Printing Office, Washington, DC, p. 54, incorporated by reference herein). These pre- and postvaccination reactivities were then compared with anti-U-TAA antibody levels.

The murine monoclonal antibody directed at a monomorphic epitope of the HLA Class 1 antigens failed to react with our U-TAA preparation even at dilutions ranging from 1:5 to 1:80. An anti-U-TAA murine monoclonal antibody run simultaneously at a dilution of 1:750 developed intense color within 1 hour.

In addition, development of anti-HLA antibodies did not correlate in any way with anti-U-TAA antibody response. Only one of the 8 patients tested developed a strong anti- During the course of vaccination he developed high levels of antibody to a variety of Class I HLA's but no change in his anti-U-TAA IgG level. The anti-U-TAA IgM titer merely doubled during this period. Another patient, number 8, never developed significant anti-HLA levels, but his anti-U-TAA IgG and IgM titers rose 6.5-fold and 3.5 fold respectively during the course of vaccination. Four other patients exhibited 2 to 4-fold increases in their anti-U-TAA IgM levels without evidencing induction of anti-HLA antibodies.

EXAMPLE XXV

Anti-KLH IgG Antibody Response: To determine whether or not the antibody response to MCV detected in melanoma patients by ELISA was specific to U-TAA, the same serum samples (pre- and post-MCV) were reacted against KLH as the target antigen. Results presented in Table 4 denote that the majority of the patients (14/15) had detectable levels of anti-KLH antibodies before MCV treatment. These antibody levels increased by greater than 2-fold in only two patients after administration of MCV. In other patients, the anti-KLH levels either remained more or less the same or decreased. There was no concordance between the increase in anti-KLH and the anti-U-TAA antibodies (IgG or IgM) in response to MCV.

TABLE 4

Anti-KLH Antibody Levels in Melanoma Patients Before and After MCV Treatment as Assessed by ELISA

| | Anti-KLH titer[a] | | Weeks |
|---|---|---|---|
| Patient # | Pre-MCV | Post-MCV | Post-MCV |
| 1 | 400 | 480 | 4 |
| 2 | 460 | 62 | 4 |

TABLE 4-continued

Anti-KLH Antibody Levels in Melanoma Patients Before and After MCV Treatment as Assessed by ELISA

| Patient # | Anti-KLH titer[a] | | Weeks |
| --- | --- | --- | --- |
| | Pre-MCV | Post-MCV | Post-MCV |
| 3 | <20 | 4,000 | 2 |
| 4 | 68 | 20 | 8 |
| 5 | 260 | 940 | 4 |
| 6 | 150 | 105 | 12 |
| 7 | 60 | 600 | 8 |
| 8 | 580 | 780 | 4 |
| 9 | 400 | 190 | 20 |
| 10 | 280 | 850 | 6 |
| 11 | 290 | 250 | 4 |
| 12 | 1,000 | 1,050 | 12 |
| 13 | 140 | 240 | 16 |
| 14 | 330 | 110 | 4 |
| 15 | 125 | 96 | 16 |

[a]Reciprocal of the titer was determined from the point on the serum dilution curve that exhibited 0.05 O.D.

EXAMPLE XXVI

Time Course of Antibody Response: Four of the 11 anti-U-TAA IgM responders developed ≧2-fold elevations in these antibody levels 2 to 6 weeks following the first vaccination, 6 after 7 to 16 weeks, and 1 after 20 weeks of immunization. Median time to anti-U-TAA IgM response was 8 weeks. Anti-U-TAA IgM titers remained elevated from 4 to >20 weeks with a median of 8 weeks in these 11 patients.

Three of the 6 patients mounting good anti-U-TAA IgG responses demonstrated ≧2-fold elevations in these titers 4 to 8 weeks following the first vaccination, one responded after 20 weeks and 2 required 40 weeks of vaccination to produce IgG responses. Median time to response was 14 weeks. The responses in these 6 patients lasted from 4 to >40 weeks, with a median of >10 weeks.

EXAMPLE XXVII

Stage of Disease and Prior Anti-M-TAA Response: Of the 15 patients evaluated in this study, 11 had disease confined to the lymph nodes or locoregional subcutaneous tissues, while 4 had distant metastases. All 4 patients with visceral metastases (3 with pulmonary metastases and 1 with a liver metastasis) mounted good anti-U-TAA IgG responses. Prior to vaccination, these anti-U-TAA IgG levels ranged from 1:1149 to 1:2816 (mean 1:2184±362). Postvaccination the titers peaked at 1:5000 to 1:14,848 with a mean of 1:8777±2117, a 4-fold increase for the group.

Anti-melanoma-TAA antibody levels from sequential serum samples were available for all 15 patients evaluated in this study (Gupta, R. K. et al., Proc. Amer. Soc. Clin. Oncol. 6:249 (1987) incorporated by reference herein). Eight of these 15 patients had mounted good anti-M-TAA antibody responses with MCV. Augmentation of anti-melanoma-TAA antibody levels did not correlate with augmentation of anti-U-TAA IgG levels ($R^2$=0.279). Overall, the anti-U-TAA response rate (IgM and/or IgG) is higher for M-TAA responders than for M-TAA non-responders, but the difference is not significantly different ($X^2$, P>0.3).

EXAMPLE XXVIII

Detection of U-TAA in the Urine of Patients with Breast, Colon and Lung Carcinomas: Urine samples obtained from patients suffering from carcinoma of the breast, colon or lung were analyzed for the presence of U-TAA using the double determinant EIA that employed murine monoclonal AD1-40F4 and baboon polyclonal anti-U-TAA IgG as described in Example IX. The incidence of the presence of detectable levels of U-TAA is listed in Table 5. These incidences are quite comparable with that of melanoma patients (63.4%).

TABLE 5

Incidence of U-TAA in urine of patients with carcinoma of the breast, colon and lung by the double determinant EIA.

| Histologic Type | # Tested | # Positive | % Positive |
| --- | --- | --- | --- |
| Breast Carcinoma | 14 | 9 | 64.3 |
| Colon Carcinoma | 13 | 9 | 69.2 |
| Lung Carcinoma | 7 | 3 | 42.8 |
| Sarcoma | 17 | 10 | 58.8 |
| Normal | 77 | 2 | 2.6 |
| Melanoma | 115 | 73 | 63.4 |

*Murine monoclonal antibody AD1-40F4 was used to capture the antigen and baboon polyclonal antibody to detect the captured antigen as described in Example IX. An EIA value of greater than 0.68 was considered positive.

EXAMPLE XXIX

Monitoring of Malignancy Using U-TAA Levels in Urine of Cancer Patients: Urine samples collected sequentially in a prospective manner from 31 melanoma patients treated by curative surgery were analyzed for U-TAA level by the double determinant EIA as described in Example IX with the following modification. The samples were heated at 100° C. in a boiling water bath for 2.5 min, cooled in an ice water bath for 5 min. and mixed with equal volume (200 μl) of 0.025M phosphate buffered saline supplement with 0.5% Tween-20. One hundred microliters of these mixtures were tested in the capture assay. Of the 31 patients, the U-TAA ELISA value of 10 patients remained negative (<0.68 $OD_{405}$) during the course of their monitoring for one year. Of these, only one (10%) has thus far had clinically detectable recurrence of the disease (Table 6). Recurrence in this patient occurred 24 weeks after entering the study. In contrast, the urine samples of 21 of 31 patients became U-TAA positive (>0.6 $OD_{405}$). Of these U-TAA positive patients, 12 (57%) have developed clinically detectable recurrence within 0 to 24 weeks). In view of the U-TAA positive results, this group of patients can be considered at high risk of recurrence. Analysis of sequential urine samples of patients with other malignancy can be used to monitor subclinical recurrence of the disease.

TABLE 6

Relationship between detection of U-TAA in urine of melanoma patients and recurrence of clinically detectable disease in a prospective study of one year.

| U-TAA | # of Patients with recurrence | # of Patients without recurrence | Total |
| --- | --- | --- | --- |
| Negative | 1 | 9 | 10 |
| Positive | 12 | 9* | 21 |
| TOTAL | | | 31 | p <0.05 by students t-test
*patients with high risk of recurrence.

EXAMPLE XXX

Stimulation of U-TAA Expression by Interferons: Modulation of the major histocompatibility antigens has been associated with tumorigenicity (Hayashi, H. et al., Cell 43:263–267, (1985) incorporated by reference herein). The evidence indicates that reduction or absence of class I antigen expression reduces immune recognition of tumor cells, allowing them to escape immune destruction. Treatment of tumor cells which have reduced or no expression of class I HLA with interferon has resulted in reduced tumorigenicity (Tanaka, K. K. et al., Science (Wash. DC) 228:26–30 (1985); Eager, K. B. et al., Proc. Natl. Acad. Sci. USA 82:5525–5529 (1985) incorporated by reference herein).

It is known that treatment of human cultured tumor cells with interferon often increases the expression of histocompatibility antigens (class I) and modulates (increases or decreases) the expression of tumor antigens (Imai, K. et al., J. Immunol. 127:505–509; Giacomini, P. et al., J. Immunol. 133:1649–1655; Perosa, F. et al., J. Immunol. 138:2202–2207 (1987) each of which is incorporated by reference herein). We treated three melanoma cell lines —UCLA-SO-M10, UCLA-SO-M24, and UCLA-SO-M101—with gamma and alpha-interferon to determine if this affected the level of U-TAA expression. The cells of each cell line were cultured in RPMI-10% FCS with and without supplementation with 500 units/ml of the interferons at 37° for 96 hrs. After treatment, the cells were harvested by scrapping, washed twice with RPMI-10% FCS, and assessed for the amount of U-TAA. A competitive ELISA utilizing allogeneic antibody and purified U-TAA was used. The allogeneic antibody, before and after absorption with the varying number of melanoma cells which had been grown in the presence and absence of interferon, was reacted with the purified U-TAA. Purified U-TAA (0.06 µg/ml) was used as the standard blocker to generate the standard inhibition curve in the ELISA.

Figure 10A:
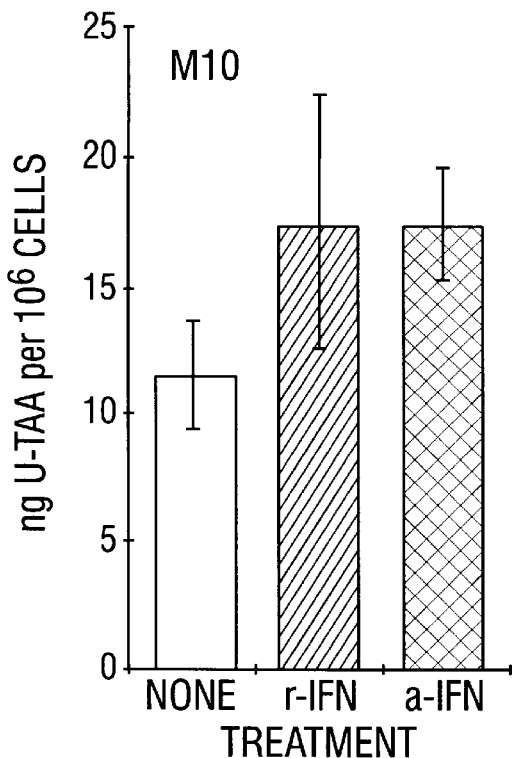
FIG. 10 shows the effect of gamma and alpha interferon on the level of U-TAA expression by three melanoma cell lines (UCLA-SO-M10, UCLA-SO-M24, and UCLA-SO-M101). Cells were cultured in RPMI-10% FCS medium with and without 500 units/ml of gamma and alpha interferon for 96 hours. U-TAA level was determined by the competitive ELISA using allogeneic antibody and purified U-TAA (0.06 mg/ml).
Figure 10B:
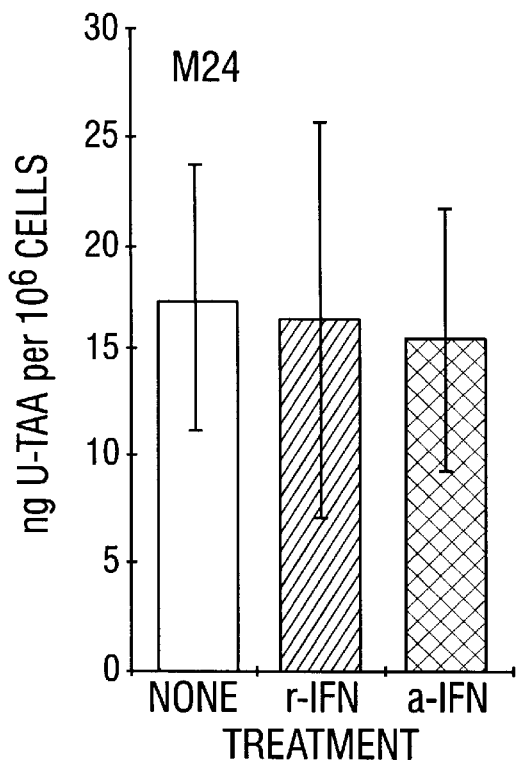
Figure 10C:
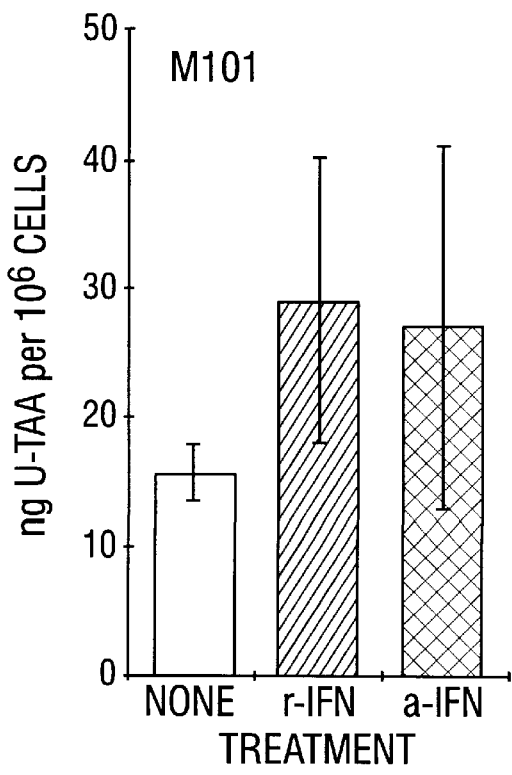

The expression of U-TAA by UCLA-SO-M10 and UCLA-SO-M101 cell lines was increased by growing the cells in the presence of either gamma interferon or alpha interferon. The expression of U-TAA by UCLA-SO-M24, however, was not affected by treatment with either interferon (FIG. 10). As a control, the expression of HLA-DR antigen was determined by reacting the cells with $^{125}$I-labeled monoclonal antibody (anti-HLA-DR) in a suspension assay. Binding of radiolabeled antibody by cells of all three cultures grown in the presence of the interferons was significantly higher (2 to 3 times) than those grown in its absence.

EXAMPLE XXXI

U-TAA is a Cell Surface Antigen: Randomly selected sera from MCV patients who had demonstrated high anti-U-TAA antibody titers in ELISA were tested by immunofluorescence for antibodies capable of binding to the surface of cultured melanoma cells. Sera demonstrating strong membrane fluorescence were tested further by using the indirect membrane immunofluorescence method to determine if U-TAA on the cell surface was responsible for part of this reactivity. Serum samples were serially diluted and incubated for 30 minutes at 37° C. and 30 minutes at 4° C. with equal volume (50 µl) of PBS alone (negative control) or PBS with 1 µg of U-TAA. Cultured UCLA-SO-M 24 melanoma cells were harvested by treatment with versene (0.05 mM sodium EDTA, 0.014 M NaCl, 0.5 mM M KCl and 0.55 mM dextrose) and 0.25% trypsin. The harvested cells were washed 3 times with Hank's balanced salt solution (HBSS), containing 0.01% human serum albumin and resuspended in HBSS-albumin at a concentration of 5×10$^4$ cells/ml. Fifty microliters of the cell suspension were mixed with 50 µl of melanoma serum at various dilutions and incubated at 37° C. for one hour and at 4° C. for one hour. The cells were washed 3 times with HBSS-albumin and reacted with 50 µl of fluorescein-conjugated goat anti-human immunoglobulin at 23° C. for 20 minutes. After washing, the cells were resuspended in 25 µl of 50% glycerol in 0.025 M PBS, placed on glass slides and examined for membrane immunofluorescence under a fluorescent microscope. The presence of 3 or more fluorescent dots on the cell membrane was considered positive for antibody. Diffuse or cytoplasmic fluorescence was not regarded as positive. The percentage of positive cells was calculated following a 50 cell count.

Figure 11:
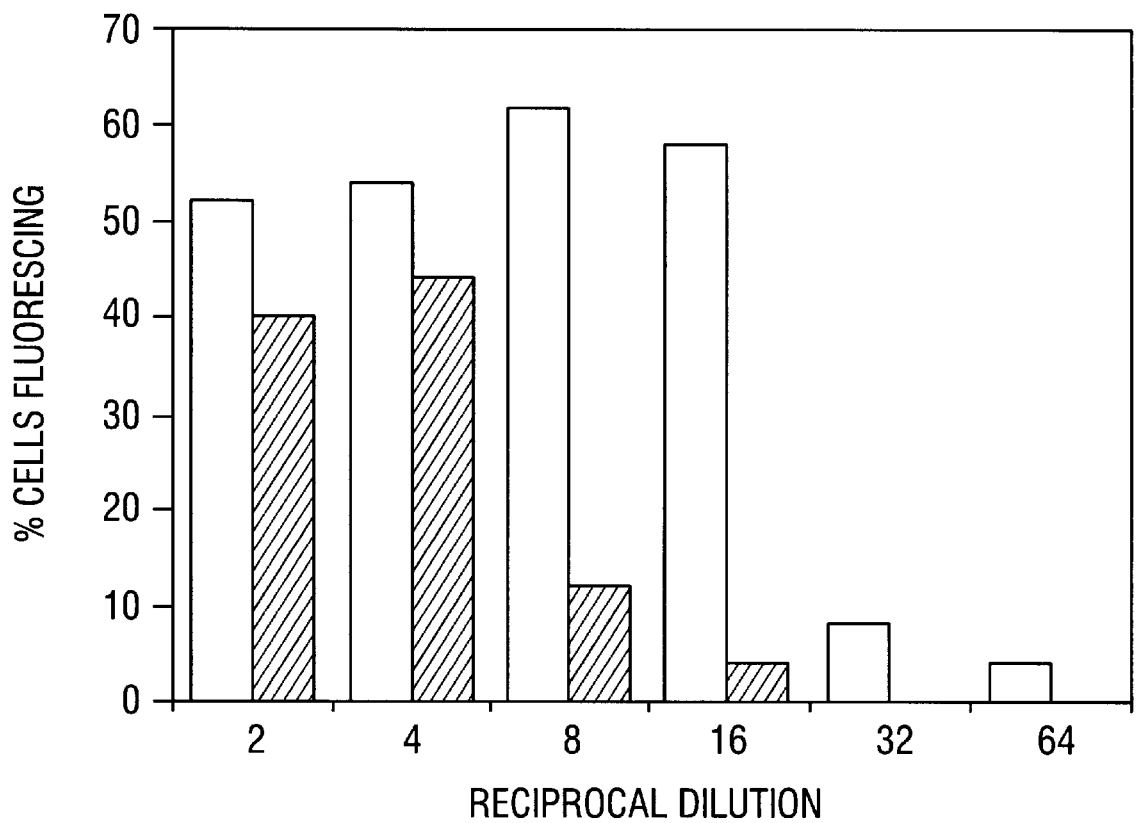
FIG. 11 shows inhibition of reactivity as observed by indirect membrane immunofluorescence between allogeneic anti-U-TAA serum and UCLA-SO-M24 (melanoma) cells by purified U-TAA. The anti-U-TAA serum at varying dilutions was preincubated with 1.0 μg U-TAA and then reacted with the melanoma cells. While the untreated antiserum maintained reactivity at 1:16 dilution (□), it was blocked by 93% after preincubation of the serum with purified U-TAA (■).

Sera with high anti-U-TAA antibody titers when tested in indirect membrane immunofluorescence showed binding of antibody to UCLA-SO-M 24 cultured melanoma cells. One serum was selected for inhibition studies with U-TAA as described above. This serum showed binding to 50–60% of melanoma cells even when diluted at 1:16. Preincubation of this serum with 1 µg of purified U-TAA resulted in a 93% reduction in the number of cells exhibiting immunofluorescence at the 1:16 serum dilution (FIG. 11). The ability of U-TAA to inhibit the binding of high titer anti-U-TAA antibody in the indirect membrane immunofluorescence assay convincingly demonstrated the expression of U-TAA on the surface cell membrane of tumor cells.

EXAMPLE XXXII

Figure 12:
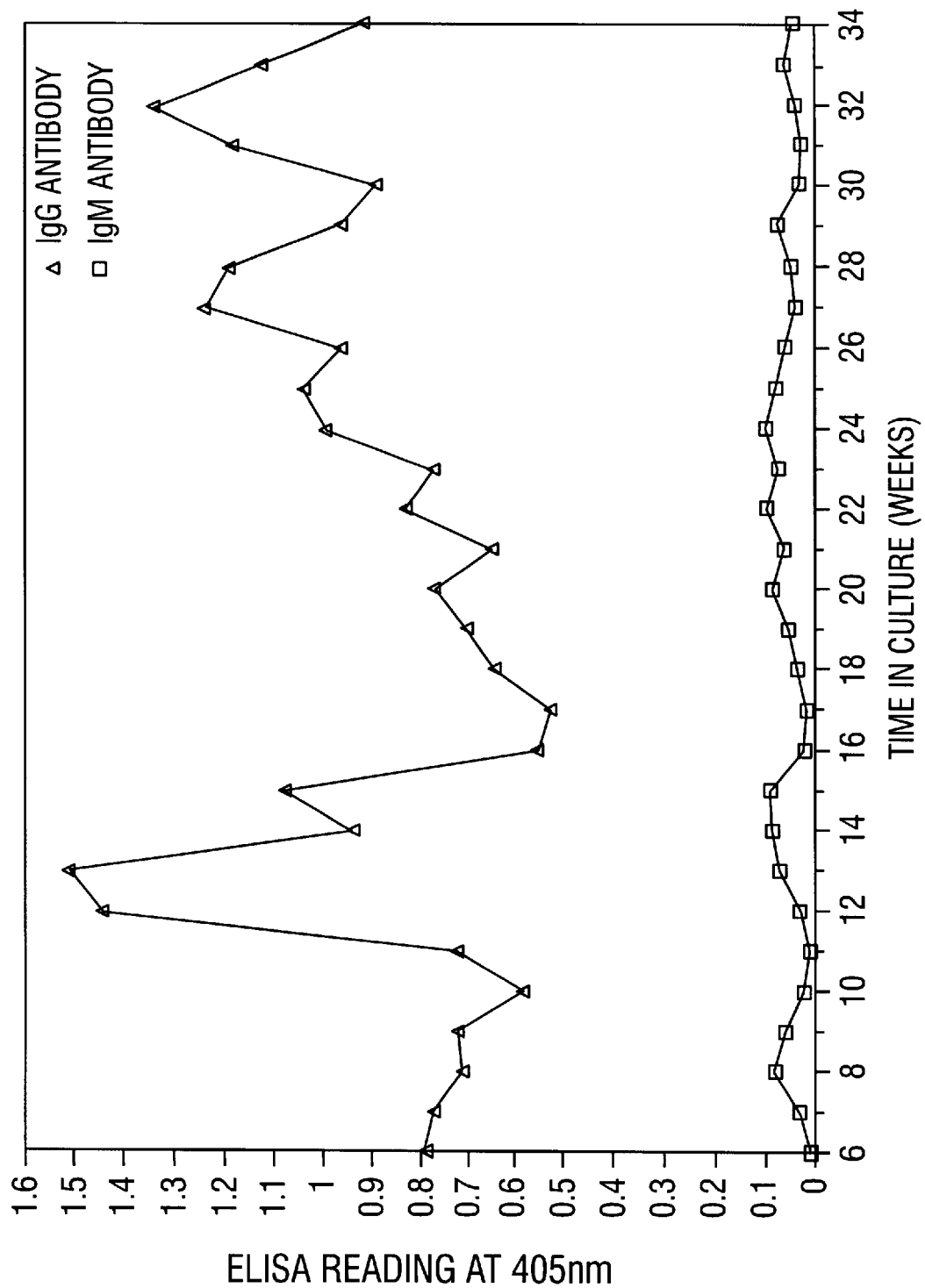
FIG. 12 shows the continued production of anti-U-TAA IgM antibody by one of the human lymphoblastoid cell lines (LCL 2) for more than six months. Cells were grown in RPMI-FCS medium. Culture supernates were collected at regular time intervals and tested in the direct ELISA using purified U-TAA (30 ng/well) for the presence of both IgG and IgM antibodies. The cultures produced IgM antibody only.

In Vitro Production of Human Antibodies to U-TAA: The Ficol-hypaque centrifugation method was used to obtain peripheral blood lymphocytes (PBL) from 30 ml of heparinized blood of cancer patients. The blood donors, who were participants in the MCV trial, were selected on the basis of their high levels of anti-U-TAA antibody. By application of the erythrocyte rosetting technique (Bakacs et al., Cellular Immunology (1977) incorporated by reference herein), T-cells were removed from the isolated PBL, which were thereby enriched for B-cells (antibody producing cells). The enriched B-cells were transformed by infecting them with Epstein Barr virus (EBV). For this purpose, enriched B-cells were suspended at a density of 10×10$^6$ cells per ml in RPMI 1640—10% FCS containing 50% supernate of the EBV producing marmaset cell line, B95-8. After overnight incubation at 37° C., the cells were washed and resuspended in the RPMI-FCS medium. Supernates from these cultures were collected at weekly intervals and tested for the presence of anti-U-TAA activity in the direct ELISA, using purified U-TAA as the target antigen (Example I). Seventeen of 35 cultures produced antibodies to U-TAA, although many cultures stopped producing the antibodies within three months. Cells from two cultures that continued to produce the antibodies for more than six months (FIG. 12) were cryopreserved at regular intervals.

Figure 13:
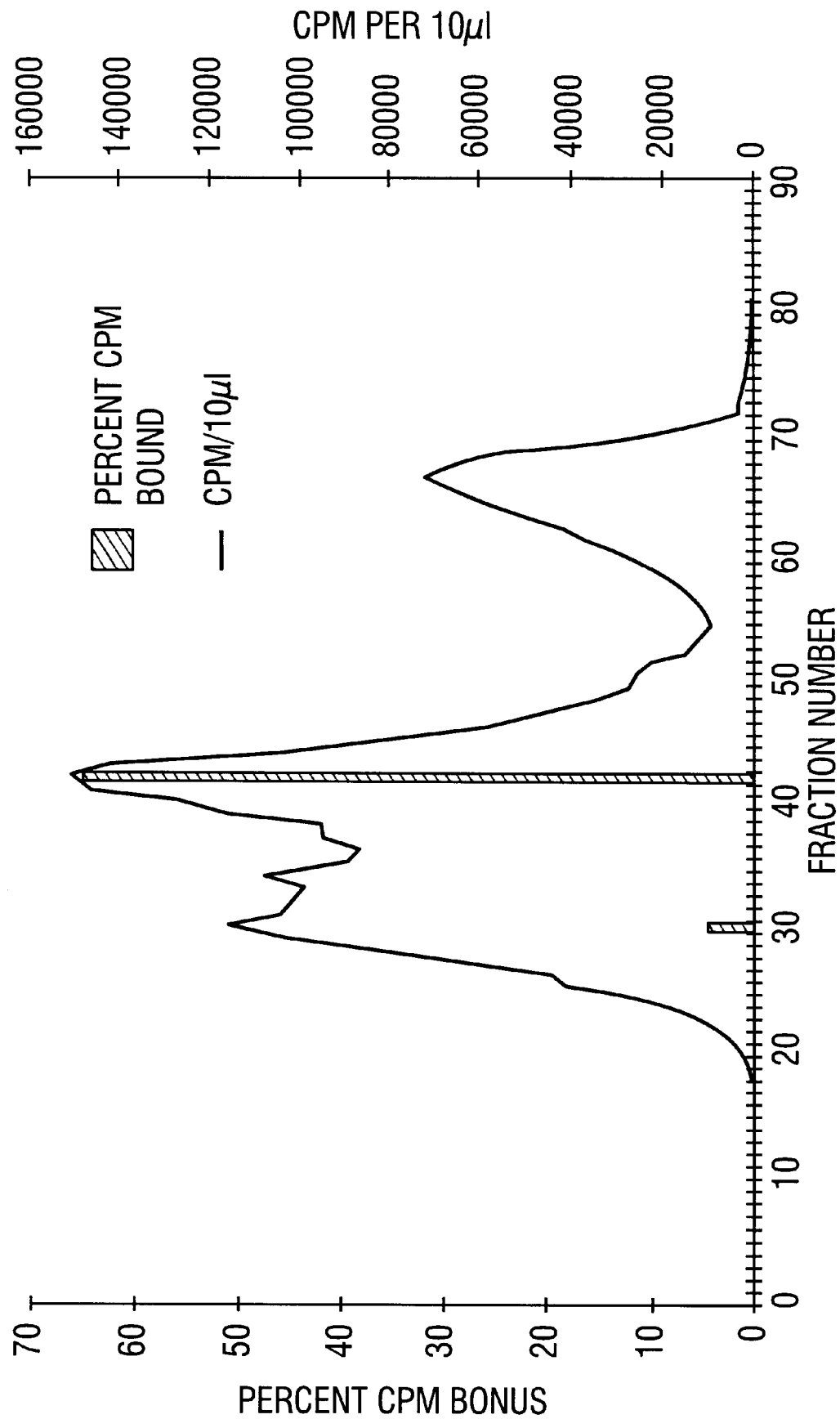
FIG. 13 shows Sephacryl S-200 elution profile of cell free NP-40 extract of intrinsically labeled ($^{14}$C-L-leucine) UCLA-SO-M14 (melanoma) cells and reactivity of various peaks with culture supernate of LCL 2 human lymphoblastoid cells. One hundred microliters of each pool was reacted with 100 μl of LCL 2 culture supernate at 37° C. for one hour. Antibody bound radioactivity was separated from the unbound radioactivity by rabbit anti human Ig immunobeads. To reduce the background, the cell free NP-40 extract was pretreated with the immunobeads. The antigenic activity was present in the peak encompassing fraction 39 through 45.

To document that the immunoreactive components recognized by the antibodies in the supernates were expressed by tumor cells, a ten fold concentrated supernate of these cultures was used as the source of in vivo produced antibody to U-TAA. Melanoma cells (UCLA-SO-M14) were cultured for five days in RPMI supplemented with $^{14}$C-L-leucine (50 uCi/ml). The cells were harvested, washed 3 times with complete RPMI-FCS medium, and extracted with 0.5% (V/V) NP-40 (Nonidet P-40) to obtain biosynthetically labeled antigen. The cell free extract was treated with immobilized wheat germ agglutinin (WGA). The bound material was eluted with chitotriase and was chromatographed through a Sephacryl S-200 column (0.5×10 cm), using 0.025M phosphate buffered saline as the eluent. Two hundred microliter fractions were collected. The elution profile was monitored by subjecting 10 μl aliquots to scintillation counting (FIG. 13). Fractions under each peak of radioactivity were pooled and reacted with 100 μl of 10× concentrated human lumphoblastoid culture supernate (in vitro produced antibody source). The radioactivity bound to the antibody was sedimented with 200 μl of 50% suspension of rabbit anti-human Ig immunobeads (Biorad Laboratories, Richmond, Calif.). As illustrated in FIG. 13, about 65% radioactivity of pool of fractions 39 to 45 bound to the human antibodies that were present in the lymphoblastoid culture supernate.

Although we have not yet succeeded in developing clones from a single cell, we have succeeded in generating subclones from lymphoblastoid cell lines (LCL 1 and LCL 2) by culturing them in soft agar (1%) using thymocytes as the feeder layers. Theoretically, colonies that develop in the soft agar are from single cells. However, this is not always true, because two or more cells often adhere to one another. Thus, monoclonality of such colonies can not be guaranteed. Analysis of two subclones (LCL 2.6 and LCL 2.11) of LCL2 culture revealed that they produce anti-U-TAA and anti-FA IgM antibodies.

Figure 14:
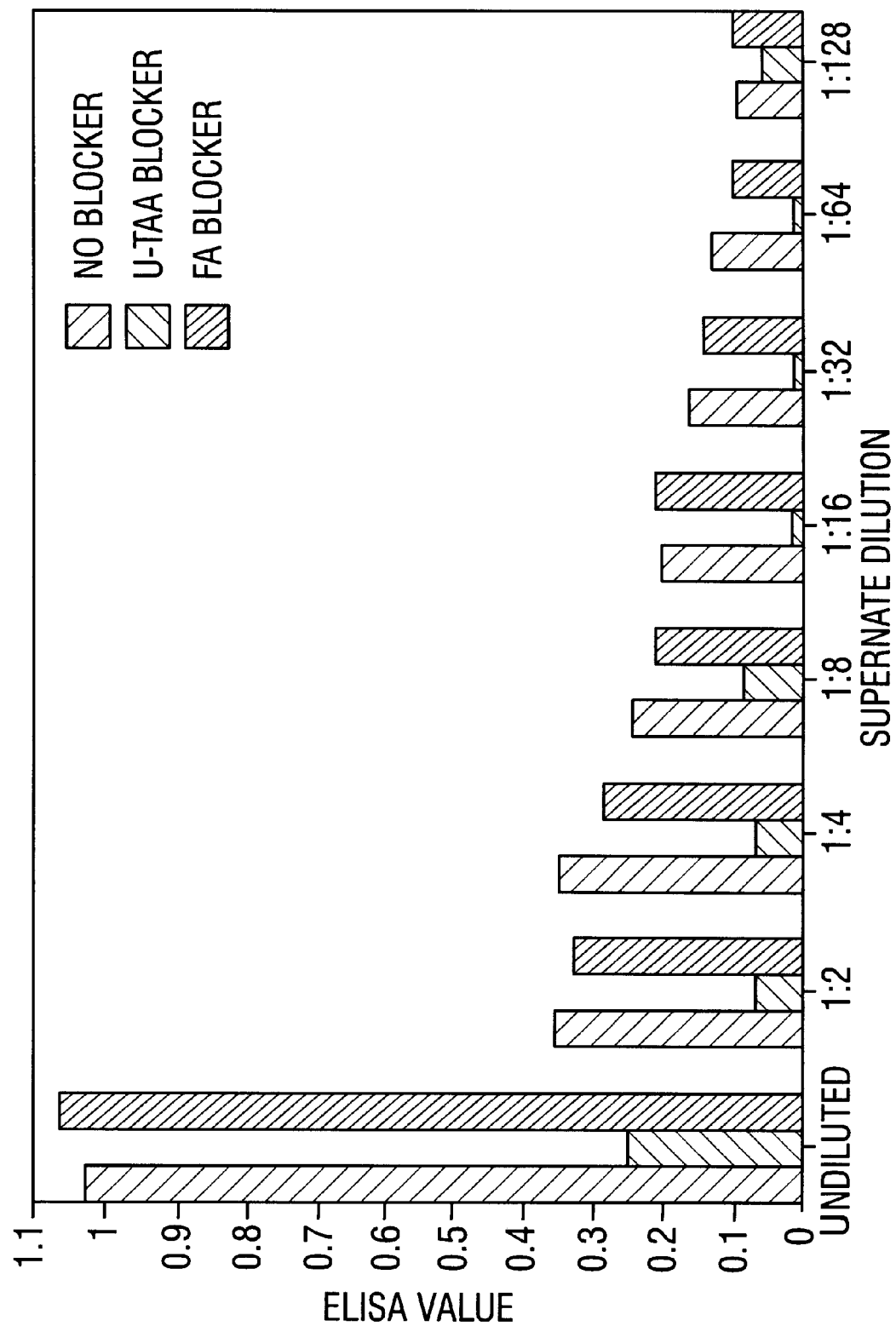
FIG. 14 shows that reactivity of LCL 2.6 culture supernate to U-TAA was blocked by U-TAA and not by FA. The supernate was reacted to U-TAA in the direct ELISA before and after blocking either with 100 μl (6 μg) of U-TAA or 100 μl (5 μg) of FA at each dilution of the supernate.
Figure 15:
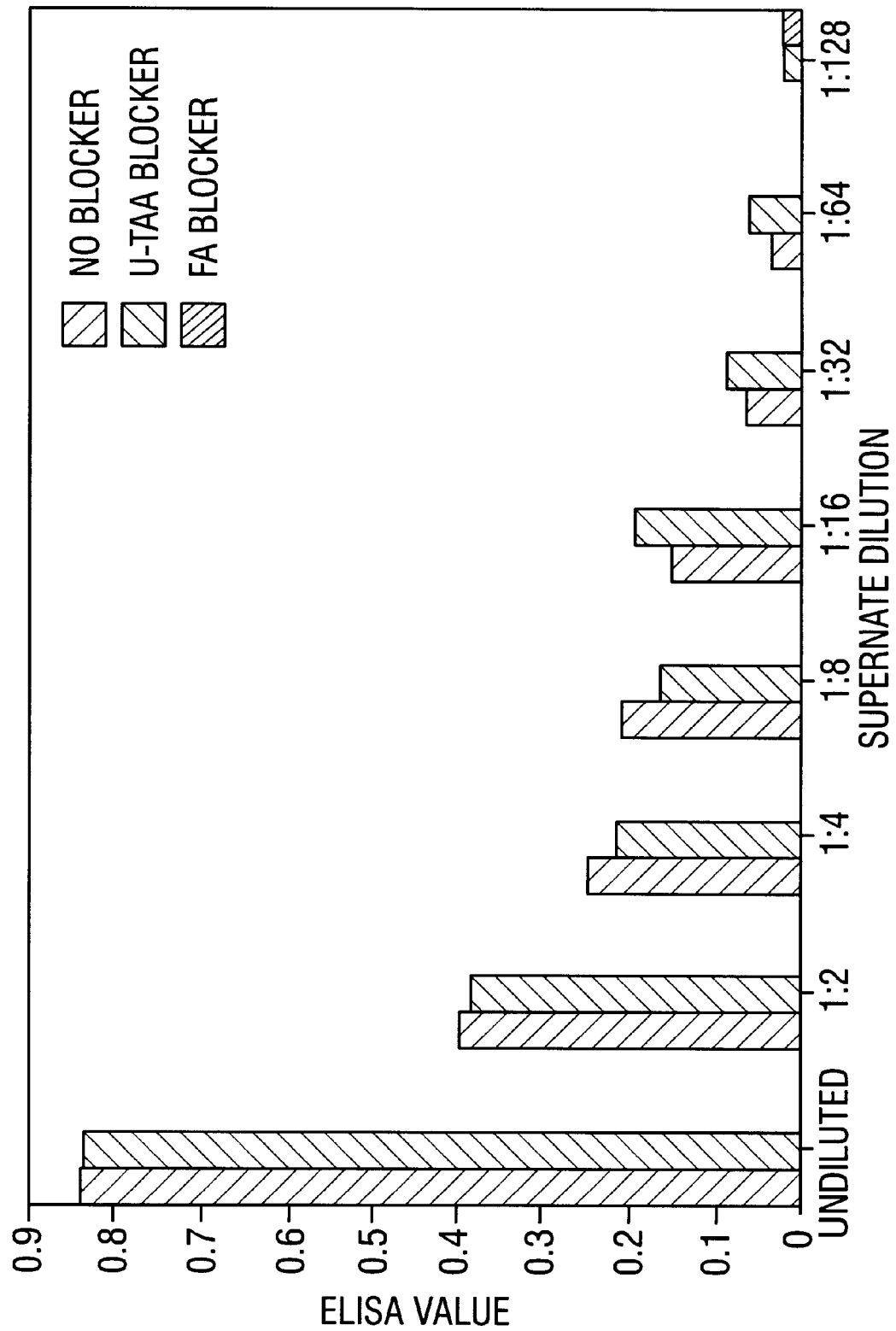
FIG. 15 shows that the reactivity of LCL 2.6 culture supernate to FA was blocked by FA and not by U-TAA. The blocking was performed as described in FIG. 14.

The specificity of the immunoreactivity of culture supernates of subclones LCL 2.6 and 2.11 was confirmed by blocking with purified FA and U-TAA and then reacting against the two target antigens in ELISA. The doubling dilution method was used to dilute serially the culture supernates. One aliquot (100 μl) of each dilution was mixed with 0.025 M phosphate buffer supplemented with 0.15 M NaCl and 0.5% Tween-20 as an unblocked control; a second aliquot was blocked with an equal volume (100 μl) of FA (0.05 mg/ml); and a third aliquot was reacted with U-TAA (0.06 mg/ml). The mixtures were incubated at 37° C. for one hour. Anti-U-TAA and anti-FA antibody levels in each of the mixtures to U-TAA and FA were determined by ELISA. Data presented in FIGS. 14 and 15 show that the reactivity of culture supernates of subclone LCL 2.6 to U-TAA was blocked by U-TAA and not by FA. Also, its reactivity to FA was blocked by FA and not by U-TAA. Similar results were observed when culture supernates of another subclone, LCL 2.11, were used as the source antibody. These results clearly show that, while the subclones LCL 2.6 and LCL 2.11 are not monoclonal at this point and time, they are producing anti-U-TAA (IgM) antibody. Subsequent subcloning of these subclones should produce clones that are monoclonal in nature.

EXAMPLE XXXIII

Detection of U-TAA that is Present in the Form of Immune Complexes in Sera of Cancer Patients: Because U-TAA is immunogenic in cancer patients, it elicits immune response. Thus, antibodies to U-TAA circulate in the blood of cancer patients, especially when the tumor burden is minimal. These antibodies may react with U-TAA on tumor cell surface. We have documented the presence of antibodies on tumor cell surfaces and determined that they react with tumor antigens specifically (Gupta, R. K. and Morton, D. L, Contemporary Topics in Immunobiology 15:1053 (1984) incorporated by reference herein). The tumor bound antibodies can be considered evidence for their immunologic interaction in vivo with corresponding antigens. The antigen-antibody (immune) complexes formed on the cell surface may be internalized by the cell or released into surroundings by the process of antigen modulation, capping, and shedding (Leong S. P. L. et al., Cancer Res. 39:2125 (1979) incorporated by reference herein). Other possible mechanisms for release of tumor antigens into circulation include cell death, surface bleeding, sublethal autolysis, and secretion from cells (Price, M. R. and Robins, R. W., Immunological Aspects of Cancer, pp. 155 (1978) incorporated by reference herein). The antigens shed into circulation combine with humoral antibodies and result in the formation of circulating immune complexes. Thus, numerous efforts have been made by various investigators with some success to utilize immune complexes as a marker for immunodiagnosis and immunoprognosis of human cancer. However, the antigenic nature of the complexes was unknown and correlations with the clinical course of the disease in cancer patients have not been unequivocal. This is mainly because of the use of antigen-nonspecific immune complex detection assays.

Figure 16:
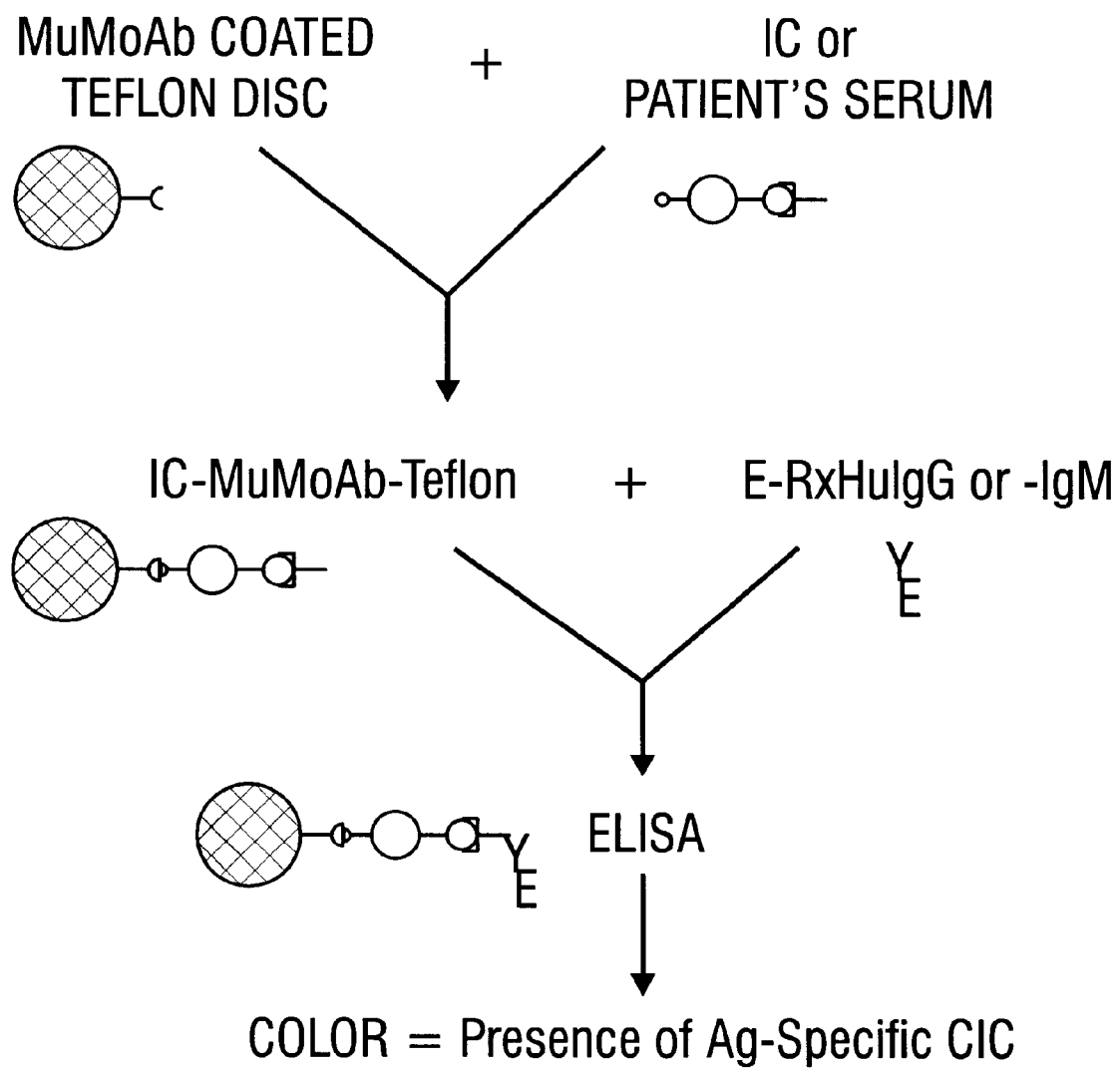
FIG. 16 illustrates schematic conceptualization of the U-TAA specific immune complex detection assay. This utilizes anti-U-TAA murine monoclonal antibody, AD1-40F4. Immune complexes react with the immobilized antibody (anti-U-TAA). The capture of human immunoglobulin via the antigen is determined by the use of rabbit or goat anti-human Ig in a manner similar to ELISA.

With the availability of murine monoclonal antibody, AD1-40F4, that recognizes 90–100 kD subunit produced by human tumor cells, we have developed an antigen-specific immune complex detection assay. The assay, as illustrated in FIG. 16, utilizes immobilization of the murine monoclonal antibody, AD1-40F4, to a solid matrix. The solid matrix could, for example, be polyvinyl or polystyrene microtiter plates or tubes or beads, Teflon discs, glass beads, or any other suitable material in any suitable physical form, e.g. glass fiber discs. The immobilization could, for example, be physical adsorption or covalent attachment by means of chemical reaction using homo- or hetero-bifunctional or multifunctional coupling agents. The immobilized monoclonal antibody is reacted with serum sample or other body fluid suspected of being comprised of U-TAA (antigen)-anti-U-TAA (antibody) complexes, or purified immune complexes from serum or other body fluid. After washing the solid matrix, the presence of human immunoglobulin on its surface is realized by enzyme or biotin labeled antibody to human immunoglobulins, general or specific for each isotype, e.g. IgG, IgM, IgA, etc. Since the murine monoclonal antibody immobilized to the solid matrix does not react with any of the serum components, the presence of human immunoglobulins on the solid matrix is due to capture of the antigen that has already reacted with the patient's antibody in vivo. Upon exposure of the conjugate reacted solid matrix to appropriate substrate, a color development indicates the presence of the antigen (U-TAA) specific immune complexes in a test sample.

We have developed the above technique in polystyrene microtiter plates (Immulon I, Dynatech Laboratories, Chantilly, Va.). Murine monoclonal antibody, AD1-40F4, was attached to the wells (100 μl at 1:300 dilution per well). Test sera (100 μl at 1:20 dilution) were added to the murine antibody sensitized wells and incubated at 37° C. for 1.0 hr. After washing, the presence of human IgG (present in the form of immune complexes) in the test wells was determined by alkaline phosphatase conjugated goat anti-human IgG and p-nitrophenyl phosphate as the substrate. The results were expressed as optical density (OD) at 405 nm. Sera from 24 melanoma patients had a mean ± SE $OD_{405}$ of 0.456±0.114. This value is significantly greater than the mean ± SE of 0.1±0.025 for sera of 32 apparently healthy normal controls (p<0.001). Using a value of greater than the mean plus 2 standard deviations (0.392 $OD_{405}$) of normal controls as an indication for the presence of U-TAA specific immune complexes, 37.5% (9/24) of the sera from melanoma patients was positive in contrast to only 6% (2/32) from normal controls (P<0.01).

Figure 17A:
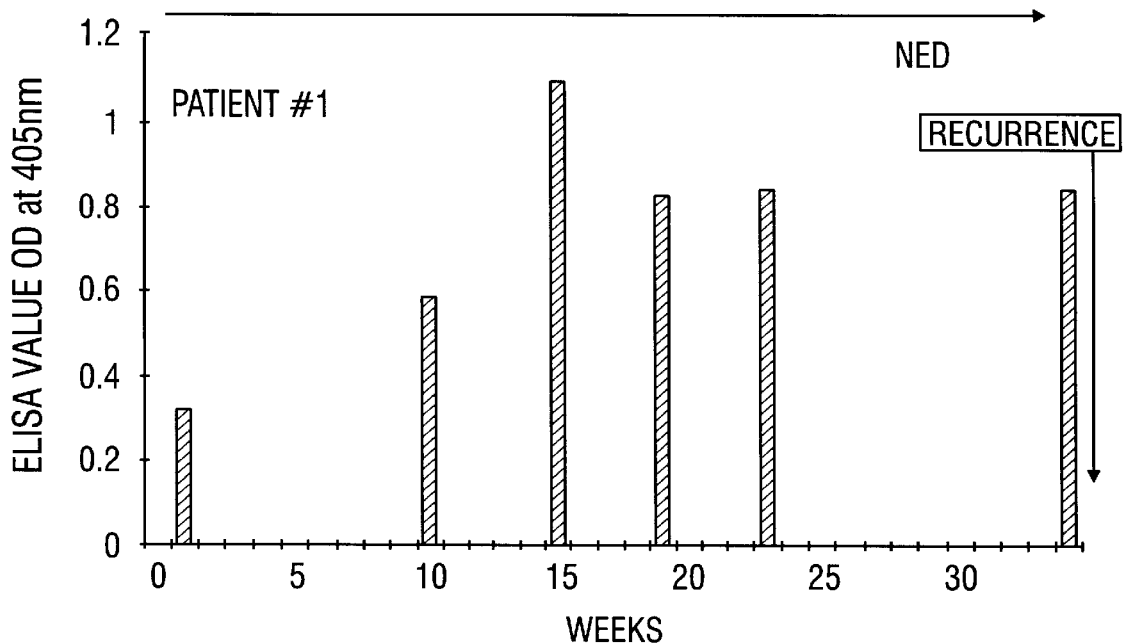
FIG. 17 shows correlation between U-TAA specific immune complex level (OD$_{405\ nm}$) and clinical course (recurrence) in patients with melanoma. The patients with stage II disease were rendered disease free by surgical resection of the primary disease and lymphadenectomy. Serum samples were obtained every time the patient visited the clinic for check-up. The serum samples were analyzed for U-TAA specific immune complexes by the assay outlined in FIG. 16. Sera were positive for U-TAA specific immune complexes in patient #1 at least 34 weeks before and in patient #2 at least 28 weeks before clinically detectable recurrence. NED=no evidence of disease.
Figure 17B:
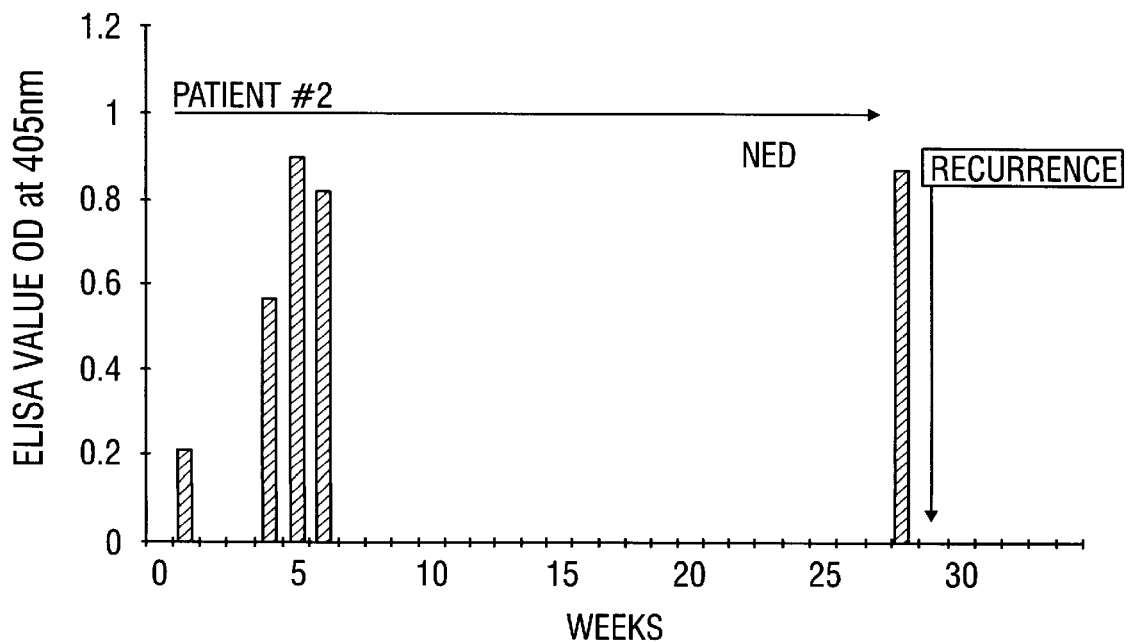

Analysis of sequentially collected serum samples during clinical course of 9 melanoma patients in a prospective study revealed that this U-TAA-specific immune complex detection assay could be used to identify patients with subclinical disease several months before their recurrence became clinically obvious. FIG. 17 illustrates this fact using data from two representative patients. Positive levels of U-TAA-specific immune complexes were detected 4 to 24 weeks (mean=14.1 weeks) before clinically detectable recurrence. Thus, this offers a useful means of identifying microscopic, subclinical disease by monitoring the presence of U-TAA-specific immune complexes in sera of surgically treated cancer patients.

EXAMPLE XXXIV

Preparation of Human Anti-idiotypic Antibodies: Large quantities of an antigen are needed for therapeutic application. The amounts obtained from cultured tumor cell extracts or from the urine of cancer patients are only enough to use in in vitro serologic and immunochemical assays. To provide an adequate supply of antigen, two approaches are available: 1) clone the gene responsible for production of U-TAA through molecular biology techniques; 2) identify EBV-transformed lymphoblastoid cells from cancer patients or human-human hybridoma of these cells that secrete anti-idiotypic antibody (internal mirror image of anti-U-TAA antibody) of anti-U-TAA. These approaches can be used successfully by those skilled in the methodology. The second approach is preferable at this time because we already had EBV-transformed lymphoblastoid cells and human-human hybridomas from lymphocytes of cancer patients.

Many of these lymphoblastoid cell lines secrete immunoglobulins but do not react with U-TAA. It is possible that some of these immunoglobulins may be anti-idiotypes of U-TAA. We have identified lymphoblastoid subclones that produce anti-U-TAA of IgM isotypes (Example XXXII). Once large quantities of these antibodies are obtained in purified form, they can be conjugated to enzymes or other suitable radionucloids and used for their ability to react with supernates of lymphoblastoid clones that do not react with U-TAA to identify clones with possible anti-idiotype reactivity. Production of anti-idiotypic antibodies to U-TAA by the positive clones can be confirmed by the blocking of anti-U-TAA with U-TAA before reacting with the suspected anti-idiotypic antibody producing clone supernates. To rule out the detection of anti-idiotypes other than internal mirror image of U-TAA, the labeled antibody will contain purified human normal serum immunoglobulin (2% V/V). The anti-idiotypes identified in this manner have a vast application for active specific immunotherapy and for chemical analysis of antigenic epitopes of U-TAA, e.g. amino acid sequence, nucleotide sequence, etc.

What is claimed is:

1. A method for inducing or enhancing in a human subject the production of antibodies reactive with the polypeptide subunit of Urinary Tumor Associated Antigen having a molecular weight of about 90 to 100 kD after reduction by β-mercaptoethanol and separation by SDS-polyacrylamide gel electrophoresis comprising administering to the subject an effective dose of a composition comprising inactivated tumor cells having a Urinary Tumor Associated Antigen on the cell surface and including therein an antigenically effective amount of GM-2, GD-2, Fetal Antigen, and Melanoma-Tumor Associated Antigen, and a pharmaceutically acceptable carrier.

2. A method for inducing or enhancing in a human subject the production of antibodies reactive with the polypeptide subunit of Urinary Tumor Associated Antigen having a molecular weight of about 90 to 100 kD after reduction by β-mercaptoethanol and separation by SDS-polyacrylamide gel electrophoresis comprising administering to the subject an effective dose of a polyvalent melanoma cell composition for injection, the composition comprising viable cells of one or more allogeneic melanoma cell lines which cells have been rendered incapable of proliferation in vivo and which provide to the composition an amount of melanoma associated antigens effective to stimulate an antitumor immune response, the composition including the specific melanoma associated antigens GD2 ganglioside, GM2 ganglioside, M-TAA, M-fetal antigen and M-urinary antigen in amounts effective to stimulate an immune response against each of said specific antigens, wherein the subject is afflicted with a cancer, and wherein said antigens are present in amounts effective to promote a cytotoxic or cytostatic effect upon administration of the composition to the subject.

3. The method of claim 2, wherein the cancer is selected from the group consisting of a melanoma, sarcoma and carcinoma.

4. A method for inducing or enhancing in a human subject the production of antibodies reactive with the polypeptide subunit of Urinary Tumor Associated Antigen (UTAA) having a molecular weight of about 90 to 100 kD after reduction by β-mercaptoethanol and separation by SDS-polyacrylamide gel electrophoresis, the method comprising administering to the subject an effective dose of an antigen composition in a pharmacologically acceptable carrier, diluent or adjuvant suitable for injection into the subject, the antigen composition comprising UTAA and at least one tumor associated antigen selected from the group consisting of GM-2; GD-2; Fetal Antigen; and Melanoma Tumor Associated Antigen.

5. The method of claim 4, wherein the antigen composition is further defined as including at least three antigens selected from the group consisting of GM-2, GD-2, Fetal Antigen, and MTAA.

6. The method of claim 5, wherein the antigen composition is further defined as including each of GM-2, GD-2, Fetal Antigen, and MTAA.

7. The method of claim 4, wherein the antigen composition is further defined as comprising tumor cells.

8. The method of claim 7, wherein the tumor cells are further defined as a tumor cell line.

9. The method of claim 8, wherein the tumor cell line is defined as line UCLA-SO-M10, UCLA-SO-M24, or UCLA-SO-M101.

10. The method of claim 7, wherein the tumor cells are irradiated tumor cells.

11. The method of claim 7, wherein the tumor cells are treated so as to increase their expression of antigens.

12. The method of claim 11, wherein the tumor cells are treated to increase their expression of histocompatibility antigens.

13. The method of claim 11, wherein the tumor cells are treated to increase their expression of tumor antigens.

14. The method of claim 7, wherein the tumor cells are treated with interferon.

* * * * *